United States Patent [19]

Kanai et al.

[11] Patent Number: 4,868,183
[45] Date of Patent: Sep. 19, 1989

[54] N-PYRAZINYL SUBSTITUTED P-AMINOPHENOLS

[75] Inventors: Kenichi Kanai; Kiyoto Goto; Kinji Hashimoto, all of Naruto, Japan

[73] Assignee: Otsuka Pharmaceutical Factory, Inc., Naruto, Japan

[21] Appl. No.: 75,910

[22] Filed: Jul. 20, 1987

[30] Foreign Application Priority Data

Jul. 21, 1986 [JP] Japan .................. 61-172431
Sep. 10, 1986 [JP] Japan .................. 61-213660
Feb. 20, 1987 [JP] Japan .................. 61-38595
Apr. 16, 1987 [JP] Japan .................. 61-94199

[51] Int. Cl.⁴ ............... C07D 241/20; A61K 31/495
[52] U.S. Cl. ..................... 514/255; 544/336; 544/406; 544/407; 544/408; 544/409; 544/182; 544/224; 544/239; 544/241; 544/326; 544/332; 548/128; 548/138; 548/234; 548/245; 548/246; 548/255; 548/266; 548/337; 548/375; 548/377; 549/68; 260/396 R; 514/245; 514/247; 514/256; 514/269; 514/275; 514/359; 514/361; 514/363; 514/376; 514/377; 514/380; 514/383; 514/398; 514/407; 514/445; 514/447
[58] Field of Search ............ 514/255; 544/336, 406, 544/407, 408, 409

[56] References Cited

U.S. PATENT DOCUMENTS

| | | | |
|---|---|---|---|
| 3,192,225 | 6/1965 | Spivack et al. | 260/306.8 |
| 3,201,409 | 8/1965 | Spivack et al. | 260/306.8 |
| 3,255,191 | 6/1966 | Dexter et al. | 260/248 |
| 3,299,087 | 1/1967 | Spivack et al. | 260/306.8 |
| 3,334,046 | 8/1967 | Dexter et al. | 252/47.5 |
| 3,467,666 | 9/1969 | Dexter et al. | 260/306.8 |
| 3,974,276 | 8/1976 | Barlow et al. | 514/255 |
| 4,172,082 | 10/1979 | Moore | 549/72 |
| 4,212,882 | 7/1980 | Moore | 424/275 |
| 4,543,413 | 9/1985 | Munro | 544/336 |
| 4,636,516 | 1/1987 | Kubo et al. | 548/154 |
| 4,642,347 | 2/1987 | Kreft, III et al. | 544/336 |
| 4,755,514 | 7/1988 | Ohta | 544/336 |

FOREIGN PATENT DOCUMENTS

| | | |
|---|---|---|
| 0059090 | 9/1982 | European Pat. Off. . |
| 0202157 | 11/1986 | European Pat. Off. . |
| 0211549 | 2/1987 | European Pat. Off. . |
| 0212848 | 3/1987 | European Pat. Off. . |
| 1302433 | 7/1962 | France . |
| 4267 | 10/1967 | France . |
| 42-10236 | 6/1967 | Japan . |
| 49-6378 | 2/1974 | Japan . |
| 49-10825 | 3/1974 | Japan . |
| 125171 | 10/1977 | Japan . |
| 53-141265 | 12/1978 | Japan . |
| 57-82829 | 5/1982 | Japan . |
| 57-150692 | 9/1982 | Japan . |
| 57-175171 | 10/1982 | Japan . |
| 58-57366 | 4/1983 | Japan . |
| 501998 | 11/1983 | Japan . |
| 60-155166 | 8/1985 | Japan . |
| 61-60648 | 3/1986 | Japan .. |
| 62-67022 | 3/1987 | Japan . |
| 62-67023 | 3/1987 | Japan . |
| 62-87580 | 4/1987 | Japan . |
| 62-120348 | 6/1987 | Japan . |
| 62-123180 | 6/1987 | Japan . |
| 62-132871 | 6/1987 | Japan . |
| 62-142162 | 6/1987 | Japan . |
| 1557622 | 12/1979 | United Kingdom . |

Primary Examiner—Anton H. Sutto
Assistant Examiner—E. Bernhardt
Attorney, Agent, or Firm—Armstrong, Nikaido, Marmelstein, Kubovcik & Murray

[57] ABSTRACT

Disclosed are compounds of the formula

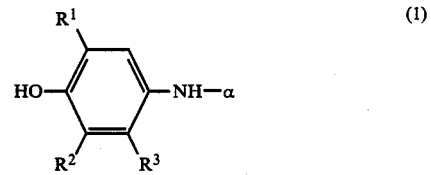

wherein:
$R^1$ is a lower alkyl group;
$R^2$ and $R^3$ are each hydrogen or lower alkyl or $R^2$ and $R^3$ taken together may form —(CH$_2$(4)— or —CH=CH—CH=CH—;
α is a 5- or 6-membered heteroaromatic ring group containing 1 to 3 hetero-atoms selected from the group consisting of nitrogen, oxygen and sulfur, or a pyrazine-N-oxide ring, pyridazine-N-oxide ring or pyrimidine-N-oxide ring group, wherein each of these heteroaromatic ring groups may optionally have 1 to 3 substituents selected from the group consisting of a lower alkyl, halogen, phenyl, lower alkoxycarbonyl, amino, lower alkoxy and hydroxy-lower alkyl, with the proviso that said 5- or 6-membered heteroaromatic ring group is not thiazolyl, isothiazolyl, pyridyl or 1,3,5-triazinyl group; or salts thereof. These compounds and salts thereof have anti-inflammatory activity and lipoxygenase-inhibitory activity.

8 Claims, No Drawings

N-PYRAZINYL SUBSTITUTED P-AMINOPHENOLS

This invention relates to novel p-aminophenol derivatives, processes for their preparation and uses thereof, especially as an anti-inflammatory agent or as an agent for inhibiting lipoxygenase.

The compounds of the present invention are p-aminophenol derivatives of the formula

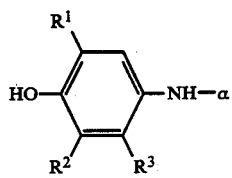

(1)

wherein:
$R^1$ is a lower alkyl group;
$R^2$ is a hydrogen atom or a lower alkyl group;
$R^3$ is a hydrogen atom or a lower alkyl group; or
$R^2$ and $R^3$ taken together may represent a group $-(CH_2)_4-$ or a group $-CH=CH-CH=CH-$; and
α is a 5- or 6-membered heteroaromatic ring group containing 1 to 3 hetero-atoms selected from the group consisting of nitrogen, oxygen and sulfur atoms, or a pyrazine-N-oxide ring, pyridazine-N-oxide ring or pyrimidine-N-oxide ring group, wherein each of these heteroaromatic ring groups may optionally have 1 to 3 substituents selected from the group consisting of a lower alkyl group, halogen atom, phenyl group, lower alkoxycarbonyl group, amino group, lower alkoxy group and hydroxy-lower alkyl group, with the proviso that said 5- or 6-membered heteroaromatic ring group is not thiazolyl, isothiazolyl, pyridyl or 1,3,5-triazinyl group; or a salt thereof.

The compounds of the formula (1) and the salts thereof according to the present invention are novel compounds undisclosed in literature. They have both an anti-inflammatory activity and an activity of inhibiting lipoxygenase. Therefore, they have therapeutic potential in treating diseased states such as acute inflammation and chronic inflammation including arthritis and rheumatism due to the reduction of inflammation, and in treating diseased states such as asthma, bronchitis and psoriasis due to the inhibition of the formation of lipoxygenase metabolites.

The compounds of the present invention exhibit such pharmaceutical activities for a prolonged period of time. They seldom cause formation of gastric ulcer and seldom cause nephropathy, and they are less toxic.

Therefore, the present invention provides a pharmaceutical composition for treating inflammation and a pharmaceutical composition for inhibiting lipoxygenase, each of the compositions comprising an effective amount of the compound of the formula (1) or a salt thereof in combination with a pharmaceutically acceptable carrier or excipient therefor.

Further, the present invention also provides a method for treating inflammation in mammals including humans comprising administering to said mammals an effective amount of the compound of the formula (1) or a salt thereof, and a method for inhibiting lipoxygenase in mammals including humans in need of such treatment comprising administering to said mammals an effective amount of the compound of the formula (1) or a salt thereof.

Of the compounds of the formula (1), preferable are those represented by the formula

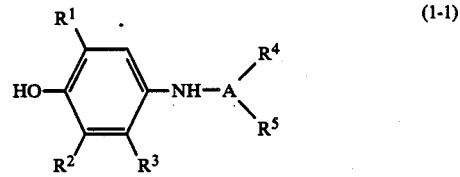

(1-1)

wherein:
$R^1$, $R^2$ and $R^3$ are as defined above;
A is pyrazinyl, pyrimidinyl, pyridazinyl, pyrazine-N-oxide ring, pyrimidine-N-oxide ring or pyridazine-N-oxide ring group;
$R^4$ is a hydrogen atom, a lower alkyl group or a halogen atom; and
$R^5$ is a hydrogen atom, lower alkyl group, halogen atom, phenyl group, lower alkoxycarbonyl group, amino group, lower alkoxy group or hydroxy-lower alkyl group; or a salt thereof.

Of the compounds of the formula (1—1), more preferable are those represented by the formula

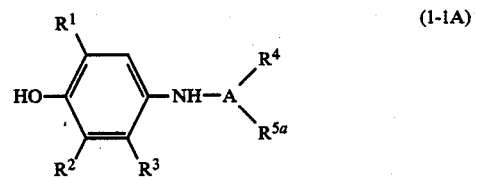

(1-1A)

wherein $R^1$ and $R^4$ are as defined in the formula (1—1), $R^2$ is a lower alkyl group, R3 is hydrogen atom, A is pyrazinyl, pyrimidinyl, pyridazinyl or pyrazine-N-oxide ring group and $R^{5a}$ is hydrogen atom, lower alkyl group, halogen atom, amino group, lower alkoxy group or hydroxy-lower alkyl group, or a salt thereof.

Typical examples of the compounds of the formula (1—1) or (1—1A) are as follows.

2,6-di-tert-butyl-4-pyrazinylaminophenol
2-isopropyl-6-tert-butyl-4-pyrazinylaminophenol
2,6-di-tert-butyl-4-[(3-pyridazinyl)amino]phenol
2,6-di-tert-butyl-4-[(6-methyl-3-pyridazinyl)amino]phenol
2,6-di-tert-butyl-4-[(6-methoxy-3-pyridazinyl)amino]phenol
2,6-di-tert-butyl-4-[(6-ethoxy-3-pyridazinyl)amino]phenol
2,6-di-tert-butyl-4-[(6-chloro-3-pyridazinyl)amino]phenol
2,6-di-tert-butyl-4-[(6-hydroxymethyl-3-pyridazinyl)amino]phenol
2,6-di-tert-butyl-4-[(4-pyridazinyl)amino]phenol
2,6-di-tert-butyl-4-[(3,6-dichloro-4-pyridazinyl)amino]pheonl
2,6-di-tert-butyl-4-[(2-pyrimidinyl)amino]phenol
2,6-di-tert-butyl-4-[(4-methyl-2-pyrimidinyl)amino]phenol
2,6-di-tert-butyl-4-[(4-pyrimidinyl)amino]phenol
2,6-di-tert-butyl-4-[(4-amino-5-pyrimidinyl)amino]phenol
2-N-[(3,5-di-tert-butyl-4-hydroxyphenyl)amino]pyrazine-1-oxide Another preferred class of the compounds of the invention includes compounds of the formula

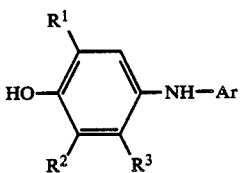

wherein;
$R^1$ and $R^2$ each represent a lower alkyl group;
$R^3$ is a hydrogen atom or a lower alkyl group; and
Ar is a 5-membered heteroaromatic ring group containing 1 to 3 hetero-atoms selected from the group consisting of nitrogen, oxygen and sulfur atoms or 1,2,3- or 1,2,4-triazinyl group, wherein each of these heteroaromatic ring groups may optionally have 1 to 3 substituents selected from the group consisting of a lower alkyl group, phenyl group and lower alkoxycarbonyl group; with the proviso that said 5-membered heteroaromatic ring group is not thiazolyl or isothiazolyl group; or a salt thereof.

Of the compounds of the formula (1-2), more preferable are those represented by the formula

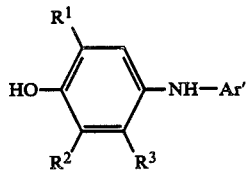

wherein $R^1$ and $R^2$ are as defined in the formula (1-2), $R^3$ is hydrogen atom, Ar' is oxazolyl, pyrazolyl, imidazolyl, thiadiazolyl, triazolyl, thienyl or 1,2,3- or 1,2,4-triazinyl group wherein these groups represented by Ar' may optionally have lower alkyl or phenyl group as the substituent.

Typical examples of the compounds of the formula (1-2) or (1-2A) are as follows.
2,6-di-tert-butyl-4-[3-pyrazolyl)amino]phenol
2,6-di-tert-butyl-4-[(2-methyl-3-pyrazolyl)amino]phenol
2,6-di-tert-butyl-4-[(2-oxazolyl)amino]phenol
2,6-di-tert-butyl-4-[(1,2,3-triazol-4-yl)amino]phenol
2,6-di-tert-butyl-4-[(1,2,4-triazol-4-yl)amino]phenol
2,6-di-tert-butyl-4-[(5-methyl-1,3,4-thiadiazol-2-yl)amino]pheonl
2,6-di-tert-butyl-4-[(2-methyl-3-thienyl)amino]phenol
2,6-di-tert-butyl-4-[(1,2,4-triazin-3-yl)amino]phenol
2,6-di-tert-butyl-4-[(3-phenyl-1,2,4-thiadiazol-5-yl)amino]phenol
2,6-di-tert-butyl-4-[(2-(imidazolyl)amino]phenol Of the compounds of the invention, another preferably compounds are those represented by the formula

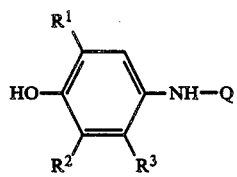

wherein $R^1$ and $R^2$ each represent lower alkyl group, $R^3$ is hydrogen atom, and Q is a substituted or unsubstituted pyrazinyl or pyridazinyl group wherein the substituent is lower alkyl group or lower alkoxy group, or Q is 1,2,4-triazinyl group.

Throughout the specification and claims, the substituents listed below have the following meanings.

Examples of lower alkyl group include straight- or branched-chain alkyl groups having 1 to 6 carbon atoms such as methyl, ethyl, propyl, isopropyl, butyl, isobutyl, tert-butyl, pentyl, hexyl and the like.

Examples of lower alkoxy group include straight- or branched-chain alkoxy groups having 1 to 6 carbon atoms such as methoxy, ethoxy, propoxy, isopropoxy, butoxy, sec-butoxy, tert-butoxy, pentyloxy, hexyloxy and the like.

Examples of halogen atom include fluorine, chlorine, bromine and iodine.

Examples of lower alkoxycarbonyl group include ($C_1$–$C_6$ alkoxy)carbonyl groups such as methoxycarbonyl, ethoxycarbonyl, propoxycarbonyl, isopropoxycarbonyl, butoxycarbonyl, tert-butoxycarbonyl, pentyloxycarbonyl, hexyloxycarbonyl and the like.

Examples of hydroxy-lower alkyl group include monohydroxy-$C_1$-$C_6$ alkyl groups such as hydroxymethyl, 1-hydroxyethyl, 2-hydroxyethyl, 3-hydroxypropyl, 2-hydroxybutyl, 3-hydroxybutyl, 4-hydroxybutyl, 5-hydroxypentyl, 2-hydroxypentyl, 3-hydroxypentyl, 4-hydroxypentyl, 6-hydroxyhexyl, 2-hydroxyhexyl, 3-hydroxyhexyl, 4-hydroxyhexyl, 1-methyl-2-hydroxyethyl, 1-methyl-2-hydroxypropyl, 1,1-dimethyl-2-hydroxyethyl and the like.

Examples of the 5- or 6-membered heteroaromatic ring group containing 1 to 3 hetero-atoms selected from the group consisting of nitrogen, oxygen and sulfur atoms include pyrrolyl group, furyl group, thienyl group, pyrazolyl group, imidazolyl group, isoxazolyl group, oxazolyl group, triazolyl group, thiadiazolyl group, oxadiazolyl group, triazinyl group, pyrazinyl group, pyrimidinyl group, pyridazinyl group and the like.

Typical examples of such 5- or 6-membered heteroaromatic ring groups containing 1 to 3 heteroatoms selected from the group consisting of nitrogen, oxygen and sulfur atoms include 1-pyrrolyl, 2-pyrrolyl, 3-pyrrolyl, 2-furyl, 3-furyl, 2-thienyl, 3-thienyl, 1-pyrazolyl, 3-pyrazolyl, 4-pyrazolyl, 5-pyrazolyl, 1-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, 1,2,3-triazol-1-yl, 1,2,3-triazol-4-yl, 1,2,3-triazol-5-yl, 1,2,4-triazol-1-yl, 1,2,4-triazol-3-yl, 1,2,4-triazol-5-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazol-2-yl, 1,2,3-oxadiazol-4-yl, 1,2,3-oxadiazol-5-yl, 1,2,4-oxadiazol-3-yl, 1,2,4-oxadiazol-5-yl, 1,3,4-oxadiazol-2-yl, 1,2,4-triazin-3-yl, 1,2,4-triazin-5-yl, 1,2,4-triazin-6-yl, 1,2,3-triazin-4-yl, 1,2,3-triazin-5-yl, pyrazinyl, 2-pyrimidinyl, 4-pyrimidinyl, 5-pyrimidinyl, 3-pyridazinyl, 4-pyridazinyl.

Examples of pyrazine-N-oxide ring, pyridazine-N-oxide ring and pyrimidine-N-oxide ring groups are pyrazine-1-oxid-2-yl, pyrazine-1-oxid-3-yl, pyrimidine-1-oxid-2-yl, pyrimidine-1-oxid-4-yl, pyrimidine-1-oxid-5-yl, pyrimidine-1-oxid-6-yl, pyridazine-1-oxid-3-yl, pyridazine-1-oxid-4-yl, pyridazine-1-oxid-5-yl, pyridazine-1-oxid-6-yl and the like.

The p-aminophenol derivatives of the formula (1) according to the invention can be prepared by various methods, as illustrated by the following reaction schemes.

<Reaction scheme 1>

Step I

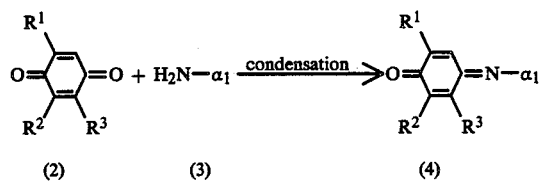

Step II

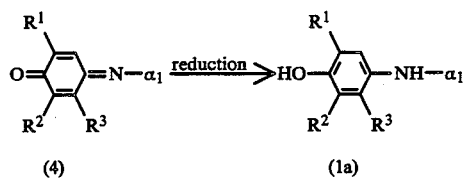

In the foregoing formulas, $R^1$, $R^2$ and $R^3$ are as defined above, and $\alpha_1$ is a 5- or 6-membered heteroaromatic ring group containing 1 to 3 hetero-atoms selected from the group consisting of nitrogen, oxygen and sulfur atoms, or a pyrazine-N-oxide, pyridazine-N-oxide or pyrimidine-N-oxide ring group, wherein each of these heteroaromatic ring groups may optionally have 1 to 3 substituents selected from the group consisting of a lower alkyl group, halogen atom, phenyl group, lower alkoxycarbonyl group, amino group and lower alkoxy group, with the proviso that said 5- or 6-membered heteroaromatic ring group is not thiazolyl, isothiazolyl, pyridyl or 1,3,5-triazinyl group.

According to the above Reaction scheme-1, the compound (1a) of the invention can be prepared by conducting Step I, i.e., the condensation reaction of a quinone derivative (2) and a heteroaromatic amine derivative (3) and Step II, i.e., reduction of the resulting condensate (4).

Of the quinone derivatives (2) to be used as one of the staring materials, alkylbenzoquinones are known or can be prepared, for example, by oxidizing alkylphenols described in Chem. Pharm. Bull., 34, 121 (1986) in accordance with the method described by D. Liotta et al in J. Org. Chem., 48, 2932 (1983). Alkylnaphthoquinones are also known or can be prepared, for example, by the method described by L. F. Fieser in J. Am. Chem., Soc., 70, 3165 (1948).

The other starting material, i.e., the heteroaromatic amine derivatives (3) are also known compounds. See, for example, G. B. Barlin, "The Chemistry of Heterocyclic Compounds" Vol. 41, Interscience, New York, 1982, Chapter 8; T. Nakagome, the same literature edited by R. N. Castle, Vol. 28, 1973, Chapter 6; D. J. Brown, the same literature, Vol. 16 , 1962, Chapter 9; and D. J. Brown, the same literature, Vol. 16 (Supplement I), 1970, Chapter 9 and the like.

The condensation reaction as shown in Step I in Reaction scheme-1 can be conducted in accordance with the method described by A. Reiker and H. Kessler in Tetrahedron, 23, 3723 (1976) by reacting the quinone derivative (2) with the heteroaromatic amine derivative (3) with heating at about 100° to 200° C.

The above condensation reaction can also be conducted by reacting the quinone derivative (2) with the heteroaromatic amine derivative (3) which acts not only as a reactant but also as an acid binder in an inert organic solvent in the presence of a halide-type Lewis acid at a temperature of between room temperature and about 120° C. Examples of the inert organic solvents are halogenated hydrocarbons such as 1,2-dichloroethane, 1,1,2-trichloroethane and chloroform, aromatic hydrocarbons such as toluene, benzene and xylene, and the like. Examples of the halide-type Lewis acids are aluminum chloride, ferric chloride, titanium tetrachloride, stannic chloride, zinc chloride and the like. An inert organic base such as pyridine, triethylamine or the like may optionally be added to the reaction system as an acid binder. There is no specific restriction on the proportions of the quinone derivative (2) and heteroaromatic amine derivative (3). However, it is preferable to use about 1 to about 10 moles, preferably about 1 to about 3 moles, of the heteroaromatic amine derivative (3) per mole of the quinone derivative (2). The foregoing reaction in which titanium tetrachloride is used can be conducted, for example, according to the method disclosed by H. Weingarten et al. in J. Org. Chem., 32, 3246 (1967).

The above condensation reaction can also be conducted by reacting the foregoing two starting materials at a temperature of between room temperature and about 100° C. in an appropriate solvent such as tetrahydrofuran or dioxane with use of a Lewis acid other than those mentioned above, such as boron trifluoride etherate. This reaction is described by J. Figueras et al in J. Org. Chem., 36, 3497 (1971).

The compound (4) obtained by the reaction of Step I can be subjected to the subsequent reduction reaction (Step II) without being isolated from the reaction mixture, or of course, as isolated therefrom.

The reduction reaction can be carried out by a usual method, for example, by placing the compound (4) into tetrahydrofuran and adding to the mixture 2 to 50 moles of sodium hydrosulfite in the form of an aqueous solution per mole of the compound (4). Depending on the type of substituent of group $\alpha_1$ included in the compound (4), the reduction reaction can alternatively be carried out, for example, by using zinc powder in acetic acid or by catalytically hydrogenating the compound (4) in the presence of a catalyst such as palladium-carbon or platinum dioxide with use of hydrogen gas, or by using sodium borohydride in a mixture of tetrahydrofuran and water.

Thus, the compound (1a) of the invention can be prepared.

Of the compounds (1) of the invention, those wherein $\alpha$ is a 5- or 6-membered heteroaromatic ring group containing 1 to 3 hetero-atoms selected from the group consisting of nitrogen, oxygen and sulfur atoms, pyrazine-N-oxide ring, pyridazine-N-oxide ring or pyzimidine-N-oxide ring group, wherein each of these heteroaromatic ring groups may optionally have 1 to 3 hydroxy-lower alkyl groups as the substituent can be prepared by various methods such as one described in Reaction scheme-2 below.

<Reaction scheme 2>

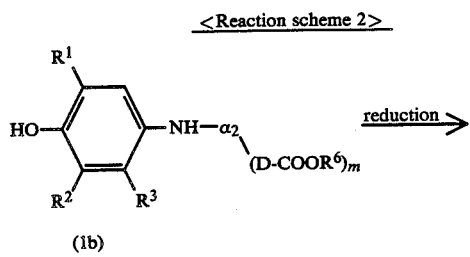

(1b)

reduction →

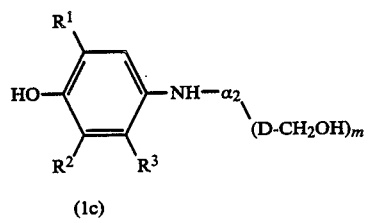

(1c)

<Reaction scheme 3>

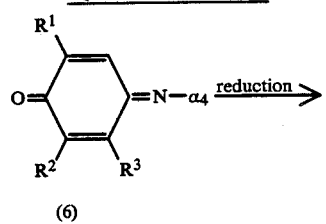

(6)

reduction →

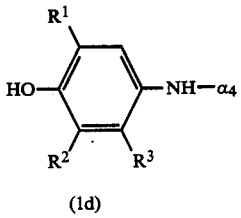

(1d)

In the foregoing formulas, $R^1$, $R^2$ and $R^3$ are as defined above; $\alpha_2$ is a 5- or 6-membered heteroaromatic ring group containing 1 to 3 hetero-atoms selected from the group consisting of nitrogen, oxygen and sulfur atoms, or a pyrazine-N-oxide ring, pyridazine-N-oxide ring or pyrimidine-N-oxide ring group, wherein each of these heteroaromatic ring groups may optionally have 1 or 2 substituents selected from the group consisting of a lower alkyl group, halogen atom, phenyl group, lower alkoxycarbonyl group, amino group and lower alkoxy group, with the proviso that said 5- or 6-membered heteroaromatic ring group is not thiazolyl, isothiazolyl, pyridyl or 1,3,5-triazinyl group; D is a straight- or branched-chain alkylene group having 1-5 carbon atoms or a single bond; $R^6$ is a lower alkyl group; and m is an integer of 1-3.

According to the reduction reaction shown in Reaction scheme-2, the compounds (1c) of the invention can be derived from the compounds (1b).

The reaction can be conducted in an inert organic solvent such as diethyl ether and tetrahydrofuran at a temperature of between about 0° C. and about 50° C., preferably between about 0° C. and around room temperature using a suitable reducing agent such as lithium aluminum hydride, aluminum hydride and diborane in an amount of about 1 to about 10 moles per mole of the compound (1b), thereby giving the desired compound (1c). This reaction is usually completed in about 0.5 to about 5 hours.

The compounds of the formula (1) wherein $\alpha$ is pyrazine-N-oxide ring, pyridazine-N-oxide ring or pyrimidine-N-oxide ring group can also be prepared by the following method as shown in Reaction scheme-3.

<Reaction scheme 3>

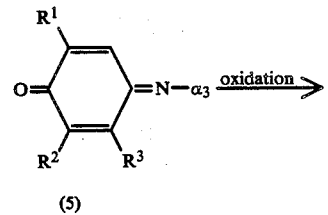

(5)

oxidation →

In the foregoing formulas, $R^1$, $R^2$ and $R^3$ are as defined above, $\alpha_3$ is a pyrazinyl, pyridazinyl or pyrimidinyl group, and $\alpha_4$ is a pyrazine-N-oxide ring, pyridazine-N-oxide ring or pyrimidine-N-oxide ring group, and each of the heteroaromatic ring groups represented by $\alpha_3$ and $\alpha_4$ may optionally have 1 to 3 substituents selected from the group consisting of a lower alkyl group, halogen atom, phenyl group, lower alkoxycarbonyl group and lower alkoxy group.

According to Reaction scheme-3, the compounds (1d) of the invention can be prepared by oxidizing the compound (5) and then reducing the resulting compound (6).

Production of the compound (6) from the compound (5), i.e., the oxidation reaction can be conducted in an inert organic solvent such as dichloromethane, chloroform and acetic acid using an organic peracid such as 3-chloroperoxybenzoic acid and peracetic acid in an amount of about 1 to about 5 moles per mole of the compound (5), at a temperature of about 0° to about 50° C. for about 5 to about 30 hours. The compounds (5) to be used as one of the starting materials in this reaction can be prepared, for example, in the same manner as in the condensation reaction shown in the foregoing Reaction scheme-1 using appropriate starting materials.

The reduction of the compound (6) subsequent to the foregoing oxidation can be conducted in the same manner as in Step II of Reaction scheme-1.

Thus the compounds (1d) can be prepared.

The compounds of the present invention obtained by the reactions represented by the foregoing schemes can be easily isolated and purified by a conventional separating method, such as solvent extraction, recrystallization or column chromatography.

The compound of the present invention thus obtained may be subjected to an addition reaction with a suitable acid compound in the usual manner, whereby the compound can be easily converted to a pharmaceutically acceptable acid addition salt, which has the same pharmacological activity as the present compound in a free state. The present invention includes such acid addition salts. Examples of acid compounds useful for forming these acid addition salts are inorganic acids such as hydrochloric acid, sulfuric acid, phosphoric acid and hydrobromic acid, and organic acids such as maleic acid, fumaric acid, malic acid, tartaric acid, citric acid, benzoic acid and benzenesulfonic acid.

The desired products of the present invention are usually administered to mammals including humans in the form of generally acceptable pharmaceutical compositions which are prepared by using diluents and excipients such as fillers, bulking agents, binders, wetting agents, disintegrating agents, surfactants, lubricants and the like. Administration unit forms of these pharmaceutical compositions of the present invention can be varied and selected so as to meet various therapeutical purposes. Typical forms of the pharmaceutical compositions can be exemplified such as tablets, pills, powders, liquids, suspensions, emulsions, granules, capsules, suppositories, injections (liquids, suspensions and others), ointments and the like.

In shaping into the form of tablets, those known as the carriers in this field can widely be applied for example, excipients such as lactose, purified sugar, sodium chloride, glucose, urea, starch, calcium carbonate, kaolin, crystalline cellulose, silicic acid and others; binders such as water, ethanol, propanol, simple syrup, a glucose solution, starch solution, gelatin solution, carboxymethyl cellulose, shellac, methyl cellulose, potassium phosphate, polyvinylpyrrolidone and others; disintegrating agents such as dried starch, sodium alginate, agar-agar powder, laminaran powder, sodium hydrogen carbonate, calcium carbonate, a fatty acid ester of polyoxyethylene sorbitan, sodium laurylsulfate, monoglyceride of stearic acid, starch, lactose and others; disintegration inhibitors such as purified sugar, stearin, cacao butter, hydrogenated oils and others; absorption accelerators such as quaternary ammonium base, sodium laurylsulfate and others; wetting agents such as glycerin, starch and others, adsorption accelerators such as starch, lactose, kaolin, bentonite, colloidal silicic acid and others; and lubricants such as purified talc powder, stearic acid salts, boric acid powder, polyethylene glycol and others can be examplified. If necessary, the tablets can further be coated with usual coating film to make them into coated tablets, for example sugar-coated tablets, gelatin film-coated tablets, enteric film-coated tablets, film-coated tablets, or double-layered tablets, multiple-layered tablets and others. In shaping into the form of pills, those known as the carriers in this field can widely be applied for example, excipients such as glucose, lactose, starch, cacao butter, hydrogenated vegetable oils, kaolin, talc and others; binders such as powdered gum arabic, powdered tragacanth gum, gelatin, ethanol and others; disintegrating agent such as laminaran, agar-agar powder and others. In shaping into the form of suppositories, those known in this field can widely be applied for example, polyethylene glycol, cacao butter, a higher alcohol, an ester of a higher alcohol, gelatin, semi-synthesized glyceride and others. Capsules are prepared in a conventional manner by admixing the compound of the invention with the foregoing various carrier and encapsulating the mixture into hard-gelatin capsules, soft-gelatin capsules, etc. In case of preparing injections, solutions, emulsions and suspensions being prepared are sterilized, and they are preferably isotonic to the blood. In preparing into the form of solutions, emulsions and suspensions, those known as the diluents in this field can widely be applied, for example water, ethanol, propylene glycol, ethoxylated isostearyl alcohol, polyoxylated isostearyl alcohol, a polyoxyethylene sorbitan fatty acid ester and others. In case of preparing isotonic solutions, suffient amount of sodium chloride, glucose or glycerin may be added to make the solution to be isotonic to the blood. The pharmaceutical compositions for injection preparation may further contain usual dissolving agents, buffer solutions, analgesic agents or the like if necessary. The pharmaceutical composition of the present invention may also contain coloring agents, preservatives, perfumes, seasoning agents, sweetening agents and others, as well as contain other medicines, if necessary. In shaping into the form of pastes, creams and gels, diluents such as white vaseline, paraffins, glycerine, cellulose derivatives, polyethylene glycols, silicones, bentonite and the like can be used.

The amount of the desired product according to the present invention to be contained as the active ingredient in the pharmaceutical composition is not specifically restricted and can be selected from a wide range, generally 1 to 70% by weight, may be used.

Administration method of the above-mentioned pharmaceutical composition is not specifically restricted and can be administered through a suitable method for the respective types of administration forms, depending upon age of the patient, distinction of the sex and others conditions, conditions of the patient and others. For example, tablets, pills, liquids, suspensions, emulsions, granules and capsules are administered orally; injections are administered intraveneously singly or as a mixture with usual injectable transfusions such as a glucose solution, an amino acids solutions, and others; and if necessary the injections are administered singly intramuscularly, intracutaneously, subcutaneously or intraperitoneally; and the suppositories are administered into rectum.

The dosage of the desired products of the present invention may suitably be selected depending upon the method for administration, age of the patient, distinction of sex and other conditions, and conditions of the symptoms, and generally the pharmaceutical composition of the invention can be administered in an amount of about 0.5 to about 500 mg/kg of the body weight/day, calculated as the compound of the invention (acitive ingredient), in 2 to 4 divided doses.

The present invention will be described in greater detail with reference to reference examples and examples. Reference examples will be given to show preparation of the starting materials for preparing the compound of the present invention. Then examples will be ggiven to show preparation of the compound of the present invention.

REFERENCE EXAMPLE 1

Preparation of 2-tert-butyl-6-isopropyl-1,4-benzoquinone

A 160 g quantity of sodium dichromate dihydrate was dissolved in a mixture of 100 ml of 97% sulfuric acid and 230 ml of water, and the solution was added to a solution of 45.0 g of 2-tert-butyl-6-isopropylphenol in 350 ml of diethyl ether with stirring at a temperature of 5°–10° C. over a period of 2.5 hours. The reaction mixture was poured into water and extracted with diethyl ether. The organic layer was washed serially with a saturated aqueous solution of sodium bicarbonate and a saturated aqueous solution of sodium chloride, dried over magnesium sulfate and concentrated. The resulting crude product was purified by silica gel column chromatography (eluent: diethyl ether-hexane=1:10), giving 12.7 g of the title compound as a pale yellow oil.

$^1$H-NMR (CDCl$_3$): δ

1.12 (d, J=6.8 Hz, 6H), 1.29 (s, 9H), 3.09 (d septet, J=6.8 Hz, 1.1 Hz, 1H), 6.45 (dd, J=2.6 Hz, 1.1 Hz, 1H), 6.53 (d, J=2.6 Hz, 1H).

REFERENCE EXAMPLE 2

Preparation of 2-tert-butyl-5,6,7,8-tetrahydro-1,4-naphthoquinone

Step 1

A 120 g quantity of 2-tert-butyl-1,4-benzoquinone was suspended in 370 ml of acetic acid, and with ice-cooling 52 g of butadiene was introduced thereinto. The mixture was allowed to stand for 48 hours in a sealed flask. Then 9 g of sodium acetate was added to the reaction mixture and the resulting mixture was refluxed with heating for 30 minutes and thereafter concentrated. The residue was dissolved in dichloromethane and the solution was washed with water, dried over magnesium sulfate, and concentrated. The resulting crude product was washed with hexane, giving 75 g of 2-tertbutyl-5,8-dihydro-1,4-naphthohydroquinone as a pale red solid.

Melting point: 122°–124° C.

$^1$H-NMR (CDCl$_3$): δ

1.39 (s, 9H), 3.23 (d, J=1.5 Hz, 4H), 4.35 (broad, 2H), 5.90 (broad s, 2H), 6.64 (s, 1H).

Step 2

A 50 g quantity of 2-tert-butyl-5,8-dihydro-1,4-naphthohydroquinone was dissolved in 300 ml of ethyl acetate, and 300 mg of platinum dioxide was added thereto. The mixture was stirred at room temperature under hydrogen atmosphere. After 5.1 l of hydrogen gas was consumed, the reaction mixture was filtered through a Celite pad and the filtrate was concentrated. The resulting crude product was washed with hexane, giving 39 g of 2-tert-butyl-5,6,7,8-tetrahydro-1,4-naphthohydroquinone as a pale red solid.

Melting point: 134°–135° C.

$^1$H-NMR (CDCl$_3$): δ

1.38 (s, 9H), 1.70–1.90 (m, 4H), 2.50–2.70 (m, 4H), 4.40 (broad s, 2H), 6.63 (s, 1H).

Step 3

A 22 g quantity of 2-tert-butyl-5,6,7,8-tetrahydro-1,4-naphthohydroquinone was suspended in 100 ml of acetic acid, and with stirring at room temperature, 10 g of nitric acid was gradually added thereto. The reaction mixture was stirred for 20 minutes at room temperature, poured into water and extracted with dichloromethane. The organic layer was washed with water, dried over magnesium sulfate and concentrated, giving 21 g of the title compound as a pale yellow solid.

Melting point: 50°–52° C.

$^1$H-NMR (CDCl$_3$): δ

1.27 (s, 9H), 1.60–1.80 (m, 4H), 2.30–2.50 (m, 4H), 6.51 (s, 1H).

EXAMPLE 1

Preparation of 2,6-di-tert-butyl-4-pyrazinylaminophenol (Compound 1)

Step I (Method I)

A 47 g quantity of 2,6-di-tert-butyl-1,4-benzoquinone and 20 g of aminopyrazine were added to 300 ml of tetrahydrofuran and dissolved therein with heating. To the solution was added a yellow suspension (which had been prepared by adding 12 ml of titanium tetrachloride dropwise with ice-cooling and stirring to a solution of 35 ml of pyridine in 200 ml of dichloroethane), and the mixture was refluxed with heating for 1 hour. To the reaction mixture was added a suspension of 70 ml of pyridine, 24 ml of titanium tetrachloride and 200 ml of dichloroethane. The resulting mixture was refluxed with heating for 2 hours. Again a suspension of 17 ml of pyridine, 6 ml of titanium tetrachloride and 100 ml of dichloroethane was added thereto and the resulting mixture was refluxed with heating for 30 minutes. Then, the reaction mixture was cooled to room temperature and filtered through a Celite pad and the insoluble materials were washed there with ethyl acetate. The filtrate was concentrated and the resulting crude product was purified by silica gel column chromatography (eluent: diethyl ether-hexane=1:10→1:1), and washed with cold hexane, thereby giving 58 g of 2,6-di-tert-butyl-4-pyrazinylimino-2,5-cyclohexadien-1-one (Compound 1a) as a yellow solid.

(Method II)

A 97.1 ml quantity of pyridine was dissolved in 944 ml of dichloroethane, and 32.9 ml of titanium tetrachloride was added thereto. The resulting mixture was refluxed with heating for 15 minutes. To the mixture were then added 132.2 g of 2,6-di-tert-butyl-1,4-benzoquinone and 57.1 g of aminopyrazine, and the mixture was refluxed with heating for 42 hours. The reaction mixture was cooled to room temperature and filtered through a Celite pad and the insoluble materials were washed there with dichloromethane. The filtrate was concentrated, and the resulting crude product was purified by silica gel column chromatography (eluent: diethyl ether-hexane=3:7), giving 82.8 g of Compound 1a.

(Method III)

A 1.62 ml quantity of pyridine was dissolved in 60 ml of dichloroethane. To the solution was added 0.89 g of aluminum chloride powder, and the mixture was refluxed with heating for 15 minutes. Then to the mixture were added 2.20 g of 2,6-di-tert-butyl-1,4-benzoquinone and 0.95 g of aminopyrazine, and the mixture was refluxed under heating for 17.5 hours. The reaction mixture was cooled to room temperature and filtered through a Celite pad and the insoluble materials were washed there with dicloromethane. The filtrate was concentrated, and the resulting crude product was purified by silica gel column chromatography (eluent: diethyl ether-hexane=3:7), giving 1.73 g of Compound 1a.

(Method IV)

A mixture of 11.02 of 2,6-di-tert-butyl-1,4-benzoquinone and 4.76 g of aminopyrazine was heated with stirring at 150° C. for 6 hours. The reaction mixture was cooled to room temperature and purified by silica gel column chromatography (eluent: diethyl ether-hexane=1:4), giving 3.95 g of Compound 1a.

The properties (melting point and $^1$H—NMR spectrum data) of Compound 1a are shown in Table 1 below. Step II A 80.1 g quantity of 2,6-di-tert-butyl-4-pyrazinylimino-2,5-cyclohexadien-1-one (Compound 1a) was dissolved in 400 ml of tetrahydrofuran. To the solution was added with ice-cooling a solution of 400 g of sodium hydrosulfite in 1500 ml of water. The mixture was stirred at room temperature for 2 hours and extracted with ethyl acetate. The organic layer was washed with a saturated aqueous solution of sodium chloride, dried over sodium sulfate and concentrated. The resulting crude product was recrystallized from ethyl acetate, giving 72.7 g of the desired title compound (Compound 1) as colorless crystals.

Table 2 below shows the properties (melting point and $^1$H—NMR spectrum data) of Compound 1.

EXAMPLES 2-31

Preparation of Compounds 2-31

Following the general procedure of Method I, II, III or IV of Step 1 of Example 1 and using 2,6-dimethyl-1,4-benzoquinone, 2,6-diisopropyl-1,4-benzoquinone, 2-tert-butyl-6-isopropyl-1,4-benzoquinone, 2,6-di-tert-butyl-1,4-benzoquinone, 2,5-di-tert-butyl-1,4-benzoquinone, 2,3,6-trimethyl-1,4-benzoquinone, 2-methyl-5,6,7,8-tetrahydro-1,4-naphthoquinone, 2-tert-butyl-5,6,7,8-tetrahydro-1,4-naphthoquinone or 2-methyl-1,4-naphthoquinone and aminodiazine derivatives, the compounds listed below in Table 1 as "Compounds 2a-31a" were prepared. Table 1 also shows the properties of these compounds.

Then following the general procedure of Step II of Example 1 and using each of Compounds 2a-31a obtained above, the compounds of the invention listed below in Table 2 as "Compounds 2-31" were prepared, respectively. Table 2 also shows the properties of these compounds.

EXAMPLE 32

Preparation of 2,6-di-tert-butyl-4-[(5-hydroxymethyl-2-pyrazinyl)amino]phenol (Compound 32)

Lithium aluminum hydride (0.14 g) was suspended in 26 ml of diethyl ether. While the suspension was stirred at room temperature, 13 ml of a solution of 0.50 g of 2,6-di-tert-butyl-4-[(5-methoxycarbonyl-2-pyrazinyl)amino]phenol (Compound 20) in tetrahydrofuran was added thereto. The resulting mixture was further stirred at room temperature for 4 hours. With cooling on an ice bath 0.5 ml of water was added thereto, followed by addition of 1.4 g of magnesium sulfate, and the mixture was stirred for 15 minutes. Insoluble materials were filtered off, and the filtrate was concentrated. The resulting crude product was purified by silica gel column chromatography (eluent: methanol-chloroform=1:19), giving 0.30 g of the title compound (Compound 32) as a pale yellow solid.

Table 2 below shows the properties of this compound.

EXAMPLE 33

Preparation of Compound 33

Following the general procedure of Example 32 and using Compound 21 as starting material, the compound listed below in Table 2 as "Compound 33" was prepared. Table 2 also shows the properties of this compound.

In Tables 1 and 2 and other tables that follow, the term "Str" means "structure", the term "M.p." means "melting point" indicated in terms of ° C., and the term "decomp." means "decomposition."

TABLE 1

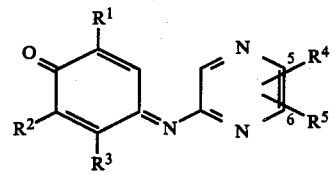

[4A]

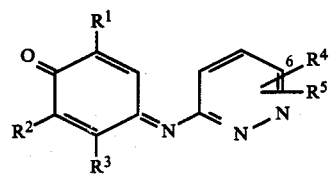

[4B]

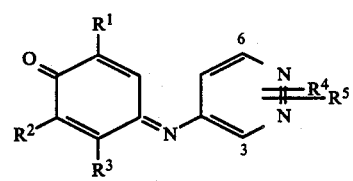

[4C]

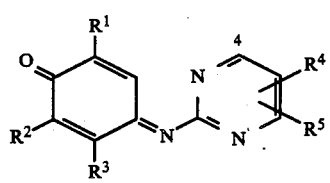

[4D]

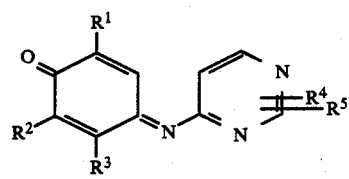

[4E]

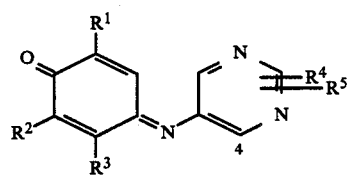

[4F]

[Compound 1a]
Str [4A]: $R^1=R^2=(CH_3)_3C$, $R^3=R^4=R^5=H$
M.p. 115.5–116.5° C.
$^1$H—NMR (CDCl$_3$): δ
1.21 (s, 9H), 1.33 (s, 9H), 6.87 (d, J= 2.5Hz, 1H), 7.04 (d, J=2.5Hz, 1H), 8.33 –8.51 (m, 3H)

[Compound 2a]
Str [4A]: $R^1=R^2=CH_3$, $R^3=R^4=R^5=H$
M.p. 114–115° C. (decomp.)
$^1$H—NMR (CDCl$_3$): δ
2.01 (d, J=1.3Hz, 3H), 2.12 (d, J=1.3 Hz, 3H), 6.93 (q, J=1.3Hz, 1H), 7.07 (q, J=1.3Hz, 1H), 8.24–8.60 (m, 3H)

TABLE 1-continued

[Compound 3a]
Str [4A]: $R^1=R^2=(CH_3)_2CH$, $R^3=R^4=R^5=H$
M.p. 72–73° C.
$^1H$—NMR (CDCl$_3$): δ
1.05 (d, J=6.8Hz, 6H), 1.19 (d, J=6.8 Hz, 6H), 2.90–3.35 (m, 2H), 6.84 (dd, J=2.6Hz, 0.9Hz, 1H), 7.00 (dd, J=2.6Hz, 0.9Hz, 1H), 8.40–8.50 (m, 3H)

[Compound 4a]
Str [4A]: $R^1=(CH_3)_3C$, $R^2=(CH_3)_2CH$, $R^3=R^4=R^5=H$
M.p. 67–69° C.
$^1H$—NMR (CDCl$_3$): δ
1.03, 1.17 (each d, J=6.8Hz, 6H), 1.22, 1.34 (each s, 9H), 2.90–3.25 (m, 1H), 6.80, 6.98 (each dd, J=2.5Hz, 1.1Hz, 1H), 6.91, 7.07 (each d, J=2.5Hz, 1H), 8.39–8.50 (m, 3H)

[Compound 5a]
Str [4A]: $R^1=R^3=(CH_3)_3C$, $R^2=R^4=R^5=H$
M.p. 128–129° C.
$^1H$—NMR (CDCl$_3$): δ
1.17 (s, 9H), 1.45 (s, 9H), 6.52 (s, 1H), 6.73 (s, 1H), 8.33 (d, J=1Hz, 1H), 8.37 (d, J=3Hz, 1H)
8.45 (dd, J=3Hz, 1Hz, 1H)

[Compound 6a]
Str [4A]: $R^1=R^2=R^3=CH_3$, $R^4=R^5=H$
M.p. 82.5–83.5° C.
$^1H$—NMR (CDCl$_3$): δ
1.96 (d, J=1.5Hz, 3H), 2.10 (d like, J=0.9Hz, 3H), 2.28 (d like, J=0.9Hz, 3H), 6.70 (q, J=1.5Hz, 1H), 8.33 (d, J=1.3Hz, 1H), 8.38 (d, J=2.6Hz, 1H), 8.45 (dd, J=2.6Hz, 1.3Hz, 1H)

[Compound 7a]
Str [4A]: $R^1=CH_3$, $R^2+R^3=(CH_2)_4$, $R^4=R^5=H$
M.p. 111–113° C.
$^1H$—NMR (CDCl$_3$): δ
1.54–1.94 (m, 4H), 1.96 (d, J=1.5Hz, 3H), 2.26–2.90 (m, 4H), 6.69 (q, J=1.5Hz, 1H), 8.22–8.62 (m, 3H)

[Compound 8a]
Str [4A]: $R^1=(CH_3)_3C$, $R^2+R^3=(CH_2)_4$, $R^4=R^5=H$
M.p. 83–84° C.
$^1H$—NMR (CDCl$_3$): δ
1.18 (s, 9H), 1.62–1.90 (m, 4H), 2.35–2.85 (m, 4H), 6.71 (s, 1H), 8.33 (d, J=1.5Hz, 1H), 8.37 (d, J=2.6Hz, 1H)
8.45 (dd, J=2.6Hz, 1.5Hz, 1H)

[Compound 9a]
Str [4A]: $R^1=CH_3$, $R^2+R^3=CH=CH-CH=CH$, $R^4=R^5=H$
M.p. 126–127° C.
$^1H$—NMR (CDCl$_3$): δ
2.13 (d, J=1.5Hz, 3H), 7.10 (q, J=1.5Hz, 1H), 7.64–7.76 (m, 2H), 8.13–8.23 (m, 1H), 8.40–8.52 (m, 4H)

[Compound 10a]
Str [4B]: $R^1=(CH_3)_3C$, $R^2=(CH_3)_2CH$, $R^3=R^4=R^5=H$
M.p. 113–114° C.
$^1H$—NMR (CDCl$_3$): δ
1.02, 1.17 (each d, J=6.8Hz, 6H), 1.21, 1.34 (each s, 9H), 2.90–3.,32 (m, 1H), 6.76, 6.97 (each m, 1H), 6.87, 7.08 (each d, J=2.5Hz, 1H), 7.28 (dd, J=8.8Hz, 1.5Hz, 1H) 7.57 (dd, J=8.8Hz, 4.7Hz, 1H), 9.05 (dd, J=4.7Hz, 1.5Hz, 1H)

[Compound 11a]
Str [4B]: $R^1=R^2=(CH_3)_3C$, $R^3=R^4=R^5=H$
M.p. 169.5–170.5° C.
$^1H$—NMR (CDCl$_3$): δ
1.20 (s, 9H), 1.34 (s, 9H), 6.82 (d, J=2.6Hz, 1H), 7.04 (d, J=2.6Hz, 1H), 7.27 (dd, J=8.6Hz, 1.5Hz, 1H), 7.56 (dd, J=8.6Hz, 4.6Hz, 1H), 9.02 (dd, J=4.6Hz, 1.5Hz, 1H)

[Compound 12a]
Str [4C]: $R^1=R^2=(CH_3)_3C$, $R^3=R^4=R^5=H$
M.p. 168.5–171° C.
$^1H$—NMR (CDCl$_3$): δ
1.19 (s, 9H), 1.34 (s, 9H), 6.48 (d, J=2.4Hz, 1H), 6.94 (dd, J=5.7Hz, 2.6Hz, 1H), 7.00 (d, J=2.4Hz, 1H), 8.78 (dd, J=2.6Hz, 1.1Hz, 1H), 9.14 (dd, J=5.7Hz, 1.1Hz, 1H)

[Compound 13a]
Str [4D]: $R^1=R^2=(CH_3)_3C$, $R^3=R^4=R^5=H$
M.p. 148–150° C.
$^1H$—NMR (CDCl$_3$): δ
1.19 (s, 9H), 1.32 (s, 9H), 6.63 (d, J=2.7Hz, 1H), 7.08 (d, J=2.7Hz, 1H),
7.12 (t, J=5.1Hz, 1H)
8.75 (d, J=5.1Hz, 2H)

[Compound 14a]
Str [4E]: $R^1=R^2=(CH_3)_3C$, $R^3=R^4=R^5=H$
M.p. 116.5–117.5° C.
$^1H$—NMR (CDCl$_3$): δ
1.26 (s, 18H), 6.80 (s, 2H),
6.96 (dd, J=6.4Hz, 1.1Hz, 1H),
8.68 (d, J=6.4Hz, 1H),
9.08 (d, J=1.1Hz, 1H)

[Compound 15a]
Str [4F]: $R^1=R^2=(CH_3)_3C$, $R^3=R^4=R^5=H$
M.p. 142–143° C.
$^1H$—NMR (CDCl$_3$): δ
1.21 (s, 9H), 1.34 (s, 9H),
6.65 (d, J=2.6Hz, 1H), 7.03 (d, J=2.6 Hz, 1H), 8.36 (s, 2H), 9.06 (s, 1H)

[Compound 16a]
Str [4A]: $R^1=R^2=(CH_3)_3C$, $R^3=R^4=H$, $R^5=5-CH_3$
M.p. 100–101.5° C.
$^1H$—NMR (CDCl$_3$): δ
1.22 (s, 9H), 1.33 (s, 9H), 2.61 (s, 3H),
6.99 (d, J=2.6Hz, 1H),
7.04 (d, J=2.6Hz, 1H), 8.34 (s, 2H)

[Compound 17a]
Str [4B]: $R^1=R^2=(CH_3)_3C$, $R^3=R^4=H$, $R^5=6-CH_3$
M.p. 157.5–159.5° C.
$^1H$—NMR (CDCl$_3$): δ
1.21 (s, 9H), 1.33 (s, 9H), 2.74 (s, 3H),
6.92 (d, J=2.6Hz, 1H), 7.03 (d, J=2.6Hz, 1H), 7.18 (d, J=8.8Hz, 1H), 7.41 (d, J=8.8Hz, 1H)

[Compound 18a]
Str [4D]: $R^1=R^2=(CH_3)_3C$, $R^3=R^4=H$, $R^5=4-CH_3$
M.p. 117.5–119.5° C.
$^1H$—NMR (CDCl$_3$): δ
1.19 (s, 9H), 1.31 (s, 9H), 2.56 (s, 3H),
6.67 (d, J=2.4Hz, 1H), 6.97 (d, J=5.1Hz, 1H),
7.07 (d, J=2.4Hz, 1H), 8.58 (d, J=5.1Hz, 1H)

[Compound 19a]
Str [4A]: $R^1=R^2=(CH_3)_3C$, $R^3=R^4=H$, $R^5 = 5-$ 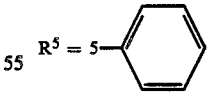

M.p. 169–170° C.
$^1H$—NMR (CDCl$_3$): δ
1.24 (s, 9H), 1.34 (s, 9H), 7.07 (s, 2H),
7.45–7.60 (m, 3H), 8.00–8.17 (m, 2H),
8.51 (d, J=1.5Hz, 1H),
8.93 (d, J=1.5Hz, 1H)

[Compound 20a]
Str [4A]: $R^1=R^2=(CH_3)_3C$, $R^3=R^4=H$, $R^5=5-COOCH_3$
M.p. 142.5–143.5° C. (decomp.)
$^1H$—NMR (CDCl$_3$): δ
1.23 (broad s, 9H), 1.31 (broad s, 9H),
4.06 (s, 3H), 6.75 (broad s, 1H),
7.00 (broad s, 1H), 8.47 (d, J=1.3Hz, 1H),
9.19 (d, J=1.3Hz, 1H)

TABLE 1-continued

[Compound 21a]
Str [4B]: R¹=R²=(CH₃)₃ C, R³=R⁴=H, R⁵=6-COOCH₃
M.p. >189.5° C. (decomp.)
¹H—NMR (CDCl₃): δ
1.19 (broad s, 9H), 1.33 (broad s, 9H), 4.09 (s, 3H), 6.78 (broad s, 1H), 7.02 (broad s, 1H), 7.36 (d, J=9.0Hz, 1H), 8.25 (d, J=9.0Hz, 1H)

[Compound 22a]
Str [4F]: R¹=R²=(CH₃)₃ C, R³=R⁴=H, R⁵=4-NH₂
M.p. 212.5-214.5° C. (decomp.)
¹H—NMR (CDCl₃): δ
1.26 (s, 9H), 1.34 (s, 9H), 5.45 (broad s, 2H), 6.98 (d, J=2.6Hz, 1H), 7.03 (d, J=2.6Hz, 1H), 7.70 (s, 1H), 8.44 (s, 1H)

[Compound 23a]
Str [4A]: R¹=R²=(CH₃)₃ C, R³=R⁴=H, R⁵=6-OCH₃
M.p. 80-82° C.
¹H—NMR (CDCl₃): δ
1.24 (s, 9H), 1.34 (s, 9H), 3.97 (s, 3H), 7.04 (d, J=2.6Hz, 1H), 7.10 (d, J=2.6Hz, 1H), 7.93 (s, 1H), 8.08 (s, 1H)

[Compound 24a]
Str [4B]: R¹=R²=(CH₃)₃ C, R³=R⁴=H, R⁵=6-OCH₃
M.p. 137.5-138° C.
¹H—NMR (CDCl₃): δ
1.23 (s, 9H), 1.33 (s, 9H), 4.16 (s, 3H), 7.01 (d, J=2.6Hz, 1H), 7.06 (d, J=2.6Hz, 1H), 7.06 (d, J=9.2Hz, 1H), 7.26 (d, J=9.2Hz, 1H)

[Compound 25a]
Str [4A]: R¹=R²=(CH₃)₃ C, R³=R⁴=H, R⁵=6-Cl
M.p. 76-78° C.
¹H—NMR (CDCl₃): δ
1.24 (s, 9H), 1.33 (s, 9H), 6.96 (d, J=2.5Hz, 1H), 7.00 (d, J=2.5Hz, 1H), 8.33 (d, J=0.5Hz, 1H), 8.41 (d, J=0.5Hz, 1H)

[Compound 26a]
Str [4B]: R¹=R²=(CH₃)₃ C, R³=R⁴=H, R⁵=6-Cl
M.p. 170-172° C.
¹H—NMR (CDCl₃): δ
1.22 (s, 9H), 1.33 (s, 9H), 6.89 (d, J=2.6Hz, 1H), 7.01 (d, J=2.6Hz, 1H), 7.25 (d, J=9.0Hz, 1H), 7.57 (d, J=9.0Hz, 1H)

[Compound 27a]
Str [4C]: R¹=R²=(CH₃)₃ C, R³=H, R⁴=3-Cl, R⁵=6-Cl
M.p. 188.5-190.5° C.
¹H—NMR (CDCl₃, 50° C.): δ
1.28 (s, 18H), 6.66 (broad s, 2H), 6.89 (s, 1H)

[Compound 28a]
Str [4B]: R¹=R²=(CH₃)₃ C, R³=R⁴=H, R⁵=6-OC₂H₅
M.p. 108-110° C.
¹H—NMR (CDCl₃): δ
1.23 (s, 9H), 1.33 (s, 9H), 1.47 (t, J=7.0Hz, 3H), 4.60 (q, J=7.0Hz, 2H), 6.99 (d, J=2.0Hz, 1H), 7.03 (d, J=9.0Hz, 1H), 7.04 (d, J=2.0Hz, 1H), 7.25 (d, J=9.0Hz, 1H)

[Compound 29a]
Str [4E]: R¹=R²=(CH₃)₃ C, R³=R⁴=H, R⁵=6-Cl
not isolated

[Compound 30a]
Str [4D]: R¹=R²=(CH₃)₃ C, R³=H, R⁴=4-CH₃, R⁵=6-CH₃
not isolated

[Compound 31a]
Str [4D]: R¹=R²=R³=CH₃, R⁴=R⁵=H
M.p. 114-115° C.
¹H—NMR (CDCl₃): δ
1.93 (d, J=1.3Hz, 3H)
2.08 (d like, J=1.0Hz, 3H)
2.29 (d like, J=1.0Hz, 3H)
6.52 (q, J=1.3Hz, 1H)
7.10 (t, J=5.0Hz, 1H)
8.72 (d, J=5.0Hz, 2H)

TABLE 2

[Structure 1A with HO-phenyl (R¹, R², R³ substituents) linked via NH to pyrazine ring with R⁴, R⁵ at positions 5, 6]

[Structure 1B with HO-phenyl linked via NH to pyridazine ring with R⁴, R⁵ at position 6]

[Structure 1C with HO-phenyl linked via NH to pyrimidine ring with R⁴, R⁵ at positions 6, 3]

[Structure 1D with HO-phenyl linked via NH to pyrimidine ring with R⁴, R⁵ at position 4]

[Structure 1E with HO-phenyl linked via NH to pyridine ring with R⁴, R⁵ at position]

[Structure 1F with HO-phenyl linked via NH to pyrazine ring with R⁴, R⁵ at position 4]

[Compound 1]
Str [1A]: R¹=R²=(CH₃)₃C, R³=R⁴=R⁵=H
M.p. 175.5-176° C.
¹H—NMR (CDCl₃): δ
1.45 (s, 18H), 5.15 (s, 1H), 6.53 (broad s, 1H), 7.14 (s, 2H), 7.88 (d, J=3Hz, 1H), 8.03 (dd, J=3Hz, 1 Hz, 1H), 8.09 (d, J=1Hz, 1H)

[Compound 2]
Str [1A]: R¹=R²=CH₃, R³=R⁴=R⁵=H (hydrochloride)
M.p. 113-114° C. (decomp.)
¹H—NMR (DMSO—d₆): δ
2.16 (s, 6H), 7.18 (s, 2H), 7.81 (broad d, TABLE 2-continued J=4 Hz, 1H), 8.09 (broad d, J=4Hz, 1H),
8.21 (broad s, 1H)
[Compound 3]
Str [1A]: $R^1=R^2=(CH_3)_2CH$,
$R^3=R^4=R^5=H$
M.p. 202-203° C.
$^1H$—NMR ($CDCl_3+CD_3OD$): δ
1.24 (d, J=6.8Hz, 12H), 3.29 (septet, J=
6.8Hz, 2H), 7.07 (s, 2H), 7.79 (d, J=
2.6Hz, 1H), 8.00-8.06 (m, 2H)
[Compound 4]
Str [1A]: $R^1=(CH_3)_3 C$, $R^2=(CH_3)_2CH$,
$R^3=R^4=R^5=H$
M.p. 191-193° C.
$^1H$—NMR ($CDCl_3+CD_3OD$): δ
1.25 (d, J=6.6 Hz, 6H), 1.42 (s, 9H),
3.17 (septet, J=6.6 Hz, 1H), 7.12 (s, 2H),
7.84 (d, J=2.9 Hz, 1H),
8.02 (dd, J=2.9 Hz, 1.5 Hz, 1H),
8.09 (d, J=1.5 Hz, 1H)
[Compound 5]
Str [1A]: $R^1=R^3=(CH_3)_3C$,
$R^2=R^4=R^5=H$
M.p. 248-248.5° C.
$^1H$—NMR ($CDCl_3+CD_3OD$): δ
1.32 (s, 9H), 1.34 (s, 9H), 6.86 (s, 1H),
7.01 (s, 1H), 7.72 (broad s, 1H),
7.83 (d, J=3Hz, 1H), 8.01 (broad d, J=3 Hz,
1H)
[Compound 6]
Str [1A]: $R^1=R^2=R^3=CH_3$, $R^4=R^5=H$
M.p. 221-223° C.
$^1H$—NMR (DMSO—$d_6$): δ
2.01 (s, 3H), 2.13 (s, 6H), 6.83 (s, 1H),
7.72 (d, J=2.6Hz, 1H), 7.84-7.95 (m,
2H), 8.02 (s, 1H), 8.42 (s, 1H)
[Compound 7]
Str [1A]: $R^1=CH_3$, $R^2+R^3=(CH_2)_4$,
$R^4=R^5=H$
M.p. 211-212° C.
$^1H$—NMR (DMSO—$d_6$): δ
1.35-1.95 (m, 4H), 2.12 (s, 3H), 2.19-
2.75 (m, 4H), 6.87 (s, 1H), 7.71 (d, J=
2.2Hz, 1H), 7.88 (s, 1H), 7.75-8.07
(m, 2H), 8.24 (s, 1H)
[Compound 8]
Str [1A]: $R^1=(CH_3)_3 C$, $R^2+R^3=(CH_2)_4$,
$R^4=R^5=H$
M.p. 260-262° C.
$^1H$—NMR (DMSO—$d_6$): δ
1.34 (s, 9H), 1.45-1.90 (m, 4H), 2.30-
2.80 (m, 4H), 6.94 (s, 1H), 7.71 (d, J=2.2
Hz, 1H), 7.79 (s, 1H), 7.90-7.95 (m, 2H),
8.31 (s, 1H)
[Compound 9]
Str [1A]: $R^1=CH_3$, $R^2+R^3=CH=CH—CH=CH$,
$R^4=R^5=H$
M.p. 235-238° C. (decomp.)
$^1H$—NMR (DMSO—$d_6$): δ
2.37 (s, 3H), 7.37-7.55 (m, 3H), 7.71-
7.99 (m, 1H), 7.79 (d, J=2.6Hz, 1H), 7.93
(dd, J=2.6Hz, 1.5Hz, 1H), 8.05 (d, J=1.5Hz,
1H), 8.19-8.31 (m, 1H), 8.94 (broad s, 2H)
[Compound 10]
Str [1B]: $R^1=(CH_3)_3 C$, $R^2=(CH_3)_2CH$,
$R^3=R^4=R^5=H$
M.p. 157-158° C.
$^1H$—NMR ($CDCl_3$): δ
1.27 (d, J=6.8Hz, 6H), 1.42 (s, 9H), 3.14
(septet, J=6.8Hz, 1H), 6.91 (dd, J=9.0Hz,
1.5Hz, 1H), 7.00 (d, J=2.6Hz, 1H), 7.05 (d,
J=2.6Hz, 1H), 7.18 (dd, J=9.0Hz, 4.4Hz,
1H), 8.58 (dd, J=4.4Hz, 1.5Hz, 1H)
[Compound 11]
Str [1B]: $R^1=R^2=(CH_3)_3C$,
$R^3=R^4=R^5=H$
M.p. 194.5-195.5° C.
$^1H$—NMR ($CDCl_3$): δ
1.44 (s, 18H), 6.91 (dd, J=9.1Hz, 1.3Hz,
1H), 7.10 (s, 2H), 7.16 (dd, J=9.1Hz,
4.4Hz, 1H), 8.57 (dd, J=4.4Hz, 1.3Hz,
1H)
[Compound 12]
Str [1C]: $R^1=R^2=(CH_3)_3C$,
$R^3=R^4=R^5=H$ (hydrochloride)
M.p. 243.5-247° C. (decomp.)
$^1H$—NMR ($CDCl_3+CD_3OD$): δ
1.44 (s, 18H), 7.07 (s, 2H), 7.16 (dd, J=
7.0Hz, 3.1Hz, 1H), 8.56 (d, J=7.0Hz,
1H), 8.76 (d, J=3.1Hz, 1H)
[Compound 13]
Str [1D]: $R^1=R^2=(CH_3)_3C$,
$R^3=R^4=R^5=H$
M.p. 144.5-145° C.
$^1H$—NMR ($CDCl_3$): δ
1.45 (s, 18H), 5.01 (s, 1H), 6.58 (t, J=
5Hz, 1H), 7.32 (s, 2H), 8.30 (d, J=5Hz,
2H)
[Compound 14]
Str [1E]: $R^1=R^2=(CH_3)_3C$,
$R^3=R^4=R^5=H$
M.p. 220-221° C.
$^1H$—NMR (DMSO—$d_6$): δ
1.40 (s, 18H), 6.64 (dd, J=7Hz, 1Hz, 1H),
6.76 (s, 1H), 7.32 (s, 2H), 8.12 (d, J=
7Hz, 1H), 8.47 (broad d, J=1Hz, 1H), 9.19
(s, 1H)
[Compound 15]
Str [1F]: $R^1=R^2=(CH_3)_3C$,
$R^3=R^4=R^5=H$
M.p. 233-235° C. (decomp.)
$^1H$—NMR (DMSO—$d_6$): δ
1.38 (s, 18H), 6.78 (s, 1H),
6.92 (s, 2H), 8.17 (s, 1H), 8.37 (s, 2H),
8.49 (s, 1H)
[Compound 16]
Str [1A]: $R^1=R^2=(CH_3)_3C$, $R^3=R^4=H$,
$R^5=5-CH_3$
M.p. 172.5-173.5° C.
$^1H$—NMR ($CDCl_3$): δ
1.43 (s, 18H), 2.41 (s, 3H), 5.11 (s, 1H),
6.41 (broad s, 1H), 7.13 (s, 2H),
7.93 (m, 1H), 8.06 (d, J=1.5Hz, 1H)
[Compound 17]
Str [1B]: $R^1=R^2=(CH_3)_3C$, $R^3=R^4=H$,
$R^5=6-CH_3$
M.p. 233-235° C.
$^1H$—NMR ($CDCl_3$): δ
1.44 (s, 18H), 2.55 (s, 3H),
6.86 (d, J=9.0 Hz, 1H), 7.06 (d, J=9.0
Hz, 1H), 7.08 (s, 2H)
[Compound 18]
Str [1D]: $R^1=R^2=(CH_3)_3C$, $R^3=R^4=H$,
$R^5=4-CH_3$
M.p. 155.5-156.5° C.
$^1H$—NMR ($CDCl_3$): δ
1.45 (s, 18H), 2.36 (s, 3H),
4.97 (s, 1H), 6.50 (d, J=6 Hz, 1H), 7.07
(broad s, 1H), 7.40 (s, 2H), 8.19 (d, J=6
Hz, 1H)
[Compound 19]
Str [1A]: $R^1=R^2=(CH_3)_3 C$, $R^3=R^4=H$,

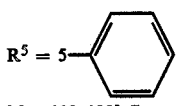

$R^5 = 5-$

M.p. 189-190° C.
$^1H$—NMR ($CDCl_3$): δ
1.45 (s, 18H), 5.13 (s, 1H), 6.51 (broad s,
1H), 7.19 (s, 2H), 7.27-7.57 (m, 3H),
7.77-7.99 (m, 2H), 8.19 (d, J=1.4Hz,
1H), 8.51 (d, J=1.4Hz, 1H)
[Compound 20]
Str [1A]: $R^1=R^2=(CH_3)_3 C$, $R^3=R^4=H$
$R^5=5-COOCH_3$
M.p. 206-207° C.
$^1H$—NMR ($CDCl_3$): δ
1.44 (s, 18H), 3.96 (s, 3H),
5.22 (s, 1H), 7.19 (s, 2H), 7.39 (broad s,

TABLE 2-continued

1H), 8.17 (d, J=1.3Hz, 1H), 8.81 (d, J=1.3 Hz, 1H)

[Compound 21]
Str [1B]: $R^1=R^2=(CH_3)_3$ C, $R^3=R^4=H$
$R^5$=6-COOCH$_3$
M.p. 215-216° C. (decomp.)
$^1$H—NMR (CDCl$_3$): δ
1.45 (s, 18H), 4.00 (s, 3H),
5.21 (broad s, 1H), 6.94 (d, J=9.5Hz, 1H),
7.12 (s, 2H), 7.88 (d, J=9.5Hz, 1H),
7.98 (broad s, 1H)

[Compound 22]
Str [1F]: $R^1=R^2=(CH_3)_3$ C, $R^3=R^4=H$
$R^5$=4-NH$_2$
M.p. 241.5-243.5° C.
$^1$H—NMR (CDCl$_3$+CD$_3$OD): δ
1.42 (s, 18H), 6.84 (s, 2H),
7.83 (s, 1H), 8.10 (s, 1H)

[Compound 23]
Str [1A]: $R^1=R^2=(CH_3)_3$ C, $R^3=R^4=H$
$R^5$=6-OCH$_3$
M.p. 222-222.5° C. (decomp.)
$^1$H—NMR (CDCl$_3$): δ
1.45 (s, 18H), 3.91 (s, 3H),
5.08 (s, 1H), 6.22 (broad s, 1H), 7.17 (s, 2H), 7.56 (s, 1H), 7.61 (s, 1H)

[Compound 24]
Str [1B]: $R^1=R^2=(CH_3)_3$ C, $R^3=R^4=H$
$R^5$=6-OCH$_3$ [1½fumarate]
M.p. 188.5-189° C. (decomp.)
$^1$H—NMR (CDCl$_3$): δ
1.40 (s, 18H), 3.91 (s, 3H),
6.63 (s, 3H, fumaric acid), 6.94 (d, J=10Hz, 1H),
7.09 (d, J=10Hz, 1H), 7.46 (s, 2H),
8.61 (broad s, 1H)

[Compound 25]
Str [1A]: $R^1=R^2=(CH_3)_3$ C, $R^3=R^4=H$
$R^5$=6-Cl
M.p. 191-192° C.
$^1$H—NMR (CDCl$_3$): δ
1.44 (s, 18H), 5.17 (s, 1H), 6.53 (broad s, 1H), 7.13 (s, 2H), 7.86 (s, 1H),
7.91 (s, 1H)

[Compound 26]
Str [1B]: $R^1=R^2=(CH_3)_3$ C, $R^3=R^4=H$
$R^5$=6-Cl
M.p. 246-246.5° C. (decomp.)
$^1$H—NMR (CDCl$_3$): δ
1.44 (s, 18H), 5.17 (broad s, 1H),
6.88 (d, J=10Hz, 1H), 7.06 (s, 2H),
7.16 (d, J=10Hz, 1H), 7.35 (broad s, 1H)

[Compound 27]
Str [1C]: $R^1=R^2=(CH_3)_3$ C, $R^3$=H,
$R^4$=3-Cl, $R^5$=6-Cl
M.p. 210-211° C.
$^1$H—NMR (CDCl$_3$): δ
1.45 (s, 18H), 5.36 (s, 1H),
6.69 (s, 2H), 7.02 (s, 2H)

[Compound 28]
Str [1B]: $R^1=R^2=(CH_3)_3$C, $R^3=R^4=H$
$R^5$=6-OC$_2$H$_5$
M.p. 176-176.5° C. (decomp.)
$^1$H—NMR (CDCl$_3$): δ
1.41 (t, J=7.0 Hz, 3H), 1.43 (s, 18H),
4.46 (q, J=7.0Hz, 2H), 6.76 (d, J=9.4Hz, 1H), 6.99 (d, J=9.4Hz, 1H),
7.03 (s, 2H)

[Compound 29]
Str [1E]: $R^1=R^2=(CH_3)_3$ C, $R^3=R^4=H$,
$R^5$=6-Cl
M.p. 235-237° C.
$^1$H—NMR (CDCl$_3$): δ
1.45 (s, 18H), 5.27 (s, 1H),
6.52 (d, J=0.9Hz, 1H), 7.06 (s, 2H),
7.47 (broad s, 1H), 8.37 (d, J=0.9Hz, 1H)

[Compound 30]
Str [1D]: $R^1=R^2=(CH_3)_3$ C, $R^3$=H,
$R^4$=4-CH$_3$, $R^5$=6-CH$_3$
M.p. 207-208.5° C.
$^1$H—NMR (CDCl$_3$): δ
1.44 (s, 18H), 2.32 (s, 6H),
4.95 (s, 1H), 6.41 (s, 1H),
7.01 (broad s, 1H), 7.48 (s, 2H)

[Compound 31]
Str [1D]: $R^1=R^2=R^3=CH_3$
$R^4=R^5=H$
M.p. 254-255° C.
$^1$H—NMR (DMSO—d$_6$): δ
1.97 (s, 3H), 2.10 (s, 3H),
2.11 (s, 3H), 6.60 (t, J=4.8Hz, 1H)
6.77 (s, 1H), 7.95 (s, 1H)
8.24 (d, J=4.8Hz, 2H), 8.54 (s, 1H)

[Compound 32]
Str [1A]: $R^1=R^2=(CH_3)_3$C, $R^3=R^4=H$,
$R^5$=5-CH$_2$OH
M.p. 177-178° C. (decomp.)
$^1$H—NMR (CDCl$_3$+CD$_3$OD): δ
1.44 (s, 18H), 4.63 (s, 2H),
7.15 (s, 2H), 7.96-8.12 (m, 2H)

[Compound 33]
Str [1B]: $R^1=R^2=(CH_3)_3$C, $R^3=R^4=H$,
$R^5$=6-CH$_2$OH
M.p. 226-228° C.
$^1$H—NMR (DMSO—d$_6$): δ
1.40 (s, 18H), 4.56 (d, J=5.8Hz, 2H),
5.32 (t, J=5.8Hz, 1H), 6.59 (broad s, 1H),
7.02 (d, J=9.3Hz, 1H), 7.39 (d, J=9.3Hz, 1H), 7.45 (s, 2H), 8.78 (broad s, 1H)

EXAMPLE 34

Preparation of 2,6-di-tert-butyl-4-(3-pyrazolylamino)phenol (Compound 34)

Step I

A mixture of 5.3 g of 2,6-di-tert-butyl-1,4-benzoquinone, 2.1 g of 3-aminopyrazole and 16 drops of acetic acid was heated with stirring at 110° C. for 15 minutes. The reaction mixture was cooled to room temperature, and then purified by silica gel column chromatography (eluent: diethyl either-chloroform=1:20), giving 5.5 g of 2,6-di-tert-butyl-4-(3-pyrazolylimino)-2,5-cyclohexadien-1-one (Compound 34a) as a pale red solid.

Table 3 below shows the structure and properties (melting point and $^1$H—NMR spectrum data) of Compound 34a.

Step II

A 1.5 g quantity of 2,6-di-tert-butyl-4-(3-pyrazolylimino)-2,5-cyclohexadien-1-one (Compound 34a) was dissolved in 21 ml of tetrahydrofuran. To the solution was added a solution of 21 g of sodium hydrosulfite in 63 ml of water. The mixture was stirred at room temperature for 30 minutes, and extracted with ethyl acetate. The organic layer was washed with a saturated aqueous solution of sodium chloride, dried over magnesium sulfate and concentrated. The resulting crude produce was washed with hexane, giving 1.3 g of title compound (Compound 34) as a colorless solid.

Table 4 below shows the structure and properties (melting point and $^1$H—NMR spectrum data) of Compound 34.

EXAMPLES 35 AND 36

Preparation of Compounds 35 and 36

Following the general procedure of Step I of Example 34, and reacting each of 2,6-diisopropyl-1,4-benzoquinone and 2-tert-butyl-6-isopropyl-1,4-benzoquinone with 3-aminopyrazole, each of the intermediate compounds (Compounds 35a and 36a) was prepared.

Table 3 below shows the structures and properties of the resulting intermediate compounds.

From each of the intermediate compounds, the title compounds (Compounds 35 and 36) were prepared following the general procedure of Step II of Example 34.

Table 4 below shows the structures and properties of Compounds 35 and 36.

EXAMPLE 37

Preparation of 2,3,6-trimethyl-4-(3-pyrazolylamino)phenol (Compound 37)

Step I

A 1.62 ml quantity of pyridine was dissolved in 60 ml of dichloroethane, and 0.55 ml of titanium tetrachloride was added thereto. The mixture was refluxed with heating for 15 minutes. Then, to the mixture were added 1.50 g of 2,3,5-trimethyl-1,4-benzoquinone and 0.83 g of 3-aminopyrazole, and the mixture was refluxed with heating for 2 hours. The reaction mixture was cooled to room temperature and filtered through a Celite pad and the insoluble materials were washed there with chloroform. The filtrate was concentrated, and the resulting crude product was purified by silica gel column chromatography (eluent: diethyl ether-hexane=1:1), giving 0.52 g of 2,3,6-trimethyl-4-(3-pyrazolylimino)-2,5-cyclohexadien-1-one (Compound 37A) as a yellow solid. Table 3 below shows the structure and properties of Compound 37a.

Step II

Following the general procedure of Step II of Example 34 and using the above Compound 37a, the title compound (Compound 37) was prepared. Table 4 below shows the structure and properties of the title compound.

EXAMPLE 38-61

Preparation of Compounds 38-61

Following the general procedure of Step I of Example 37 and reacting 2,6-di-tert-butyl-1,4-benzoquinone with appropriate heteroaromatic amine derivatives, the desired intermediate compounds listed in Table 3 below as "Compounds 38a-61a" were prepared. Table 3 below shows the structures and properties of the resulting compounds.

From each of the resulting intermediate compounds, the contemplated compounds (Compounds 38-61) were prepared following the general procedure of Step II of Example 34. Table 4 below shows the structures and properties of these compounds.

TABLE 3

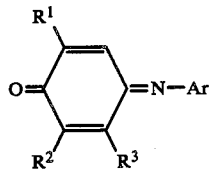

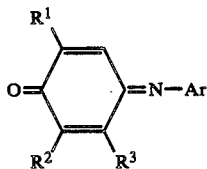

[Compound 34a]

TABLE 3-continued

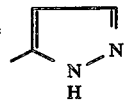

Str: $R^1 = R^2 = C(CH_3)_3$, Ar =
$R^3 = H$

M.p.: 163–165° C.
$^1$H—NMR (CDCl$_3$): δ
1.26 (s, 9H), 1.33 (s, 9H)
6.23 (d, J=2.4 Hz, 1H)
7.06 (d, J=2.6 Hz, 1H)
7.52 (d, J=2.6 Hz, 1H)
7.60 (d, J=2.4 Hz, 1H)
[Compound 35a]

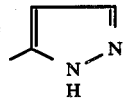

Str: $R^1 = R^2 = CH(CH_3)_2$, Ar =
$R^3 = H$

M.p.: 127–129° C.
$^1$H—NMR (CDCl$_3$): δ
1.12 (d, J=6.9 Hz, 6H)
1.17 (d, J=6.9 Hz, 6H)
3.14 (septet, d, J=6.9 Hz, 2H)
6.27 (d, J=2.3 Hz, 1H)
7.02 (d, J=2.6 Hz, 1H)
7.53 (d, J=2.6 Hz, 1H)
7.63 (d, J=2.3 Hz, 1H)
[Compound 36a]

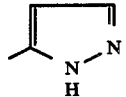

Str: $R^1 = C(CH_3)_3$, Ar =
$R^2 = CH(CH_3)_2$,
$R^3 = H$

M.p.: 141–142° C.
$^1$H—NMR (CDCl$_3$): δ
1.10, 1.16 (each d, J=6.8 Hz, 6H)
1.28, 1.33 (each s, 9H)
3.14 (broad septet, J=6.8 Hz, 1H)
6.24, 6.25 (each d, J=2.4 Hz, 1H)
6.43 (broad, 1H)
6.98, 7.47 (each dd, J=2.6 Hz, 1.1 Hz, 1H) 7.08, 7.62 (each d, J=2.6 Hz, 1H)
7.60, 7.62 (each d, J=2.4 Hz, 1H)
[Compound 37a]

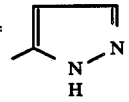

Str: $R^1 = R^2 = R^3 = CH_3$, Ar =

M.p.: 129–129.5° C.
$^1$H—NMR (CDCl$_3$): δ
2.01 (d, J=1.3 Hz, 3H)
2.07 (d like, J=1.0 Hz, 3H)
2.26 (d like, J=1.0 Hz, 3H)
5.63 (broad, 1H)
6.17 (d, J=2.0 Hz, 1H)
7.34 (q, J=1.3 Hz, 1H)
7.61 (d, J=2.0 Hz, 1H)
[Compound 38a]

TABLE 3-continued

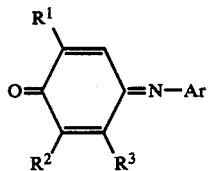

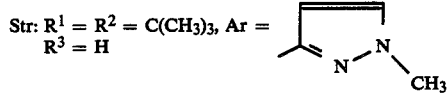

M.p.: 95–97° C.
$^1$H—NMR (CDCl$_3$): δ
1.29 (s, 9H), 1.31 (s, 9H)
3.93 (s, 3H)
6.25 (d, J=2.2 Hz, 1H)
7.03 (d, J=2.6 Hz, 1H)
7.36 (d, J=2.2 Hz, 1H)
7.79 (d, J=2.6 Hz, 1H)
[Compound 39a]

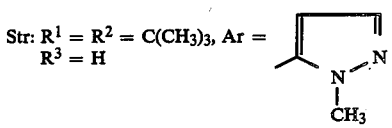

M.p.: 92–93° C.
$^1$H—NMR (CDCl$_3$): δ
1.30 (s, 9H), 1.33 (s, 9H)
3.91 (s, 3H)
5.98 (d, J=2.2 Hz, 1H)
7.01 (d, J=2.6 Hz, 1H)
7.35 (d, J=2.6 Hz, 1H)
7.52 (d, J=2.2 Hz, 1H)
[Compound 40a]

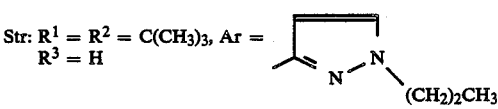

Form: oil
$^1$H—NMR (CDCl$_3$): δ
0.95 (t, J=7.3 Hz, 3H)
1.29 (s, 9H), 1.31 (s, 9H)
1.74–2.18 (m, 2H)
4.08 (t, J=6.9 Hz, 2H)
6.26 (d, J=2.3 Hz, 1H)
7.04 (d, J=2.6 Hz, 1H)
7.38 (d, J=2.3 Hz, 1H)
7.81 (d, J=2.6 Hz, 1H)
[Compound 41a]

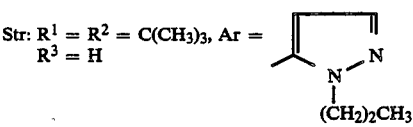

Form: oil
$^1$H—NMR (CDCl$_3$): δ
0.91 (t, J=7.4 Hz, 3H)
1.30 (s, 9H), 1.34 (s, 9H)
1.67–2.11 (m, 2H)
4.23 (t, J=7.0 Hz, 2H)
5.96 (d, J=2.0 Hz, 1H)
6.99 (d, J=2.6 Hz, 1H)
7.36 (d, J=2.6 Hz, 1H)
7.53 (d, J=2.0 Hz, 1H)
[Compound 42a]

TABLE 3-continued

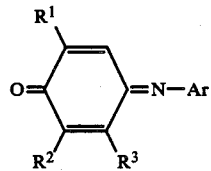

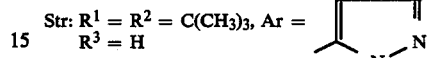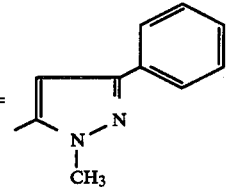

M.p.: 156–157° C.
$^1$H—NMR (CDCl$_3$): δ
1.32 (s, 9H), 1.34 (s, 9H)
3.96 (s, 3H), 6.27 (s, 1H)
7.03 (d, J=2.6 Hz, 1H)
7.30–7.60 (m, 4H)
7.74–7.85 (m, 2H)
[Compound 43a]

Str: R$^1$ = R$^2$ = C(CH$_3$)$_3$, Ar =
R$^3$ = H
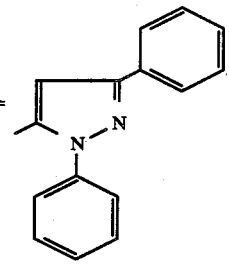

M.p.: 82–83° C.
$^1$H—NMR (CDCl$_3$): δ
1.33 (s, 18H)
6.37 (s, 1H)
7.01 (d, J=2.6 Hz, 1H)
7.36–7.51 (m, 7H)
7.72 (m, 2H)
7.90 (m, 2H)
[Compound 44a]

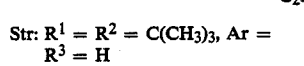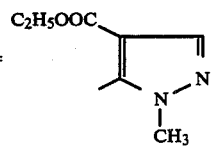

M.p.: 72–73° C.
$^1$H—NMR (CDCl$_3$): δ
1.18 (t, J=7.2 Hz, 3H)
1.20 (s, 9H), 1.34 (s, 9H)
3.74 (s, 3H)
4.13 (q, J=7.2 Hz, 2H)
6.71 (d, J=2.6 Hz, 1H)
7.04 (d, J=2.6 Hz, 1H)
7.93 (s, 1H)
[Compound 45a]

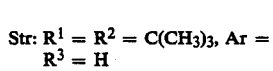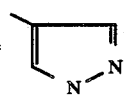

M.p.: 175–177° C. (decomp.)
$^1$H—NMR (CDCl$_3$): δ
1.31 (s, 9H), 1.32 (s, 9H)

TABLE 3-continued

[structure: R¹, R², R³ substituted quinone imine with =N-Ar]

7.04 (d, J=3.0 Hz, 1H)
7.29 (d, J=3.0 Hz, 1H)
7.66 (s, 2H)
[Compound 46a]

Str: R¹ = R² = C(CH₃)₃, Ar = (1-methylpyrazol-4-yl)
R³ = H

M.p.: 128–130° C.
¹H—NMR (CDCl₃): δ
1.30 (s, 18H), 3.95 (s, 3H)
7.00 (d, J=2.6 Hz, 1H)
7.28 (d, J=2.6 Hz, 1H)
7.44 (broad s, 1H), 7.47 (broad s, 1H)
[Compound 47a]

Str: R¹ = R² = C(CH₃)₃, Ar = (3-methyl-2-methoxycarbonylthiophene)
R³ = H

Form: oil
¹H—NMR (CDCl₃): δ
1.18 (s, 9H), 1.33 (s, 9H)
3.79 (s, 3H), 6.63 (d, J=2.6 Hz, 1H)
6.66 (d, J=5.2 Hz, 1H), 7.09 (d, J=2.6 Hz, 1H), 7.51 (d, J=5.2 Hz, 1H)
[Compound 48a]

Str: R¹ = R² = C(CH₃)₃, Ar = (2-methylpyrrol)
R³ = H

M.p.: 196.5–198.5° C.
¹H—NMR (CDCl₃): δ
1.33 (s, 9H), 1.34 (s, 9H)
6.91 (d, J=2.6 Hz, 1H)
7.15 (broad s, 1H), 7.33 (broad s, 1H)
8.76 (d, J=2.6 Hz, 1H)
[Compound 49a]

Str: R¹ = R² = C(CH₃)₃, Ar = (2-methylfuran)
R³ = H

M.p.: 88–89.5° C.
¹H—NMR (CDCl₃): δ
1.32 (s, 18H), 6.99 (d, J=2.6 Hz, 1H)
7.35 (d, J=0.9 Hz, 1H)
7.72 (d, J=0.9 Hz, 1H)
8.25 (d, J=2.6 Hz, 1H)
[Compound 50a]

Str: R¹ = R² = C(CH₃)₃, Ar = (3-methyl-5-isoxazolyl)
R³ = H

M.p.: 134.5–135° C.
¹H—NMR (CDCl₃): δ
1.25 (s, 9H), 1.31 (s, 9H)
2.46 (d, J=0.8 Hz, 3H)

TABLE 3-continued

[structure: R¹, R², R³ substituted quinone imine with =N-Ar]

5.94 (d like, J=0.8 Hz, 1H)
7.00 (d, J=2.6 Hz, 1H)
7.17 (d, J=2.6 Hz, 1H)
[Compound 51a]

Str: R¹ = R² = C(CH₃)₃, Ar = (5-methyl-1H-1,2,3-triazol-4-yl)
R³ = H

M.p.: 160–161.5° C. (decomp.)
¹H—NMR (CDCl₃): δ
1.29 (s, 9H), 1.33 (s, 9H)
7.06 (d, J=2.6 Hz, 1H)
7.72 (d, J=2.6 Hz, 1H), 7.78 (s, 1H)
[Compound 52a]

Str: R¹ = R² = C(CH₃)₃, Ar = (1,5-dimethyl-1,2,3-triazol-4-yl)
R³ = H

M.p.: 143.5–145° C. (decomp.)
¹H—NMR (CDCl₃): δ
1.32 (s, 18H), 4.14 (s, 3H)
6.97 (d, J=2.6 Hz, 1H)
7.68 (s, 1H), 8.22 (d, J=2.6 Hz, 1H)
[Compound 53a]

Str: R¹ = R² = C(CH₃)₃, Ar = (2,5-dimethyl-pyrazol)
R³ = H

M.p.: 56.5–58.5° C.
¹H—NMR (CDCl₃): δ
1.30 (s, 9H), 1.32 (s, 9H)
4.23 (s, 3H), 7.01 (d, J=2.6 Hz, 1H)
7.59 (s, 1H), 7.74 (d, J=2.6 Hz, 1H)
[Compound 54a]

Str: R¹ = R² = C(CH₃)₃, Ar = (1H-imidazol-4-yl with N=N)
R³ = H

M.p.: 190–191° C. (decomp.)
¹H—NMR (CDCl₃ + CD₃OD): δ
1.28 (s, 9H), 1.30 (s, 9H)
6.98 (d, J=2.5 Hz, 1H)
8.07 (d, J=2.5 Hz, 1H), 8.12 (s, 1H)
[Compound 55a]

Str: R¹ = R² = C(CH₃)₃, Ar = (1-methylimidazole ring)
R³ = H

M.p.: 187–188° C.
¹H—NMR (CDCl₃): δ
1.27 (s, 9H), 1.33 (s, 9H)
6.89 (d, J=2.9 Hz, 1H),
7.09 (d, J=2.9 Hz, 1H), 8.32 (s, 2H)

TABLE 3-continued

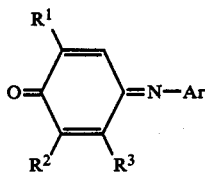

[Compound 56a]

Str: R¹ = R² = C(CH₃)₃, Ar = 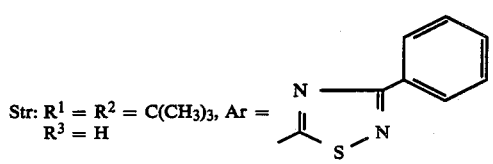
R³ = H

M.p.: 150–152° C.
¹H—NMR (CDCl₃): δ
1.29 (s, 9H), 1.34 (s, 9H), 7.02 (d,
J=2.7 Hz, 1H), 7.39–7.67 (m, 3H),
7.60 (d, J=2.7 Hz, 1H),
8.15–8.39 (m, 2H)
[Compound 57a]

Str: R¹ = R² = C(CH₃)₃, Ar = 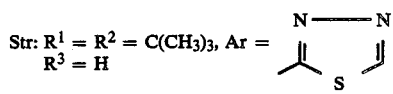
R³ = H

M.p.: 133.5–135.5° C.
¹H—NMR (CDCl₃): δ
1.28 (s, 9H), 1.33 (s, 9H)
6.98 (d, J=2.6 Hz, 1H)
7.51 (d, J=2.6 Hz, 1H), 9.10 (s, 1H)
[Compound 58a]

Str: R¹ = R² = C(CH₃)₃, Ar = 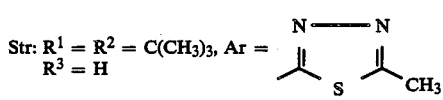
R³ = H

M.p.: 125–127° C.
¹H—NMR (CDCl₃): δ
1.28 (s, 9H), 1.32 (s, 9H), 2.78 (s, 3H), 6.96 (d, J=2.6 Hz, 1H)
7.57 (d, J=2.6 Hz, 1H)
[Compound 59a]

Str: R¹ = R² = C(CH₃)₃, Ar = 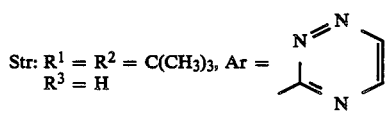
R³ = H

M.p.: 132.5–134.5° C.
¹H—NMR (CDCl₃): δ
1.21 (broad s, 9H), 1.33 (broad s, 9H)
6.67 (broad s, 1H), 7.10 (broad s, 1H)
8.66 (d, J=2.3 Hz, 1H)
9.11 (d, J=2.3 Hz, 1H)
[Compound 60a]

Str: R¹ = R² = C(CH₃)₃, Ar = 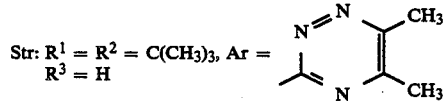
R³ = H

M.p.: 135–137° C.
¹H—NMR (CDCl₃): δ
1.21 (s, 9H), 1.33 (s, 9H), 2.59 (s, 3H), 2.73 (s, 3H), 6.83 (d, J=2.6 Hz, 1H), 7.10 (d, J=2.6 Hz, 1H)
[Compound 61a]

TABLE 3-continued

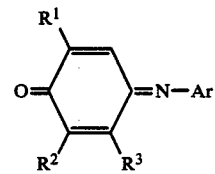

Str: R¹ = R² = C(CH₃)₃, Ar = 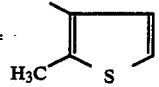
R³ = H not isolated

TABLE 4

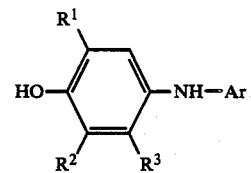

[Compound 34]

Str: R¹ = R² = C(CH₃)₃, Ar = 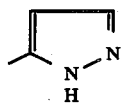
R³ = H

M.p.: 131–133° C.
¹H—NMR (CDCl₃): δ
1.41 (s, 18H),
5.90 (d, J=2.4 Hz, 1H)
6.55 (broad s, 3H)
6.98 (s, 2H)
7.28 (d, J=2.4 Hz, 1H)
[Compound 35]

Str: R¹ = R² = CH(CH₃)₂, Ar = 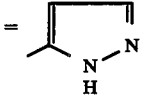
R³ = H

M.p.: 131–133° C.
¹H—NMR (CDCl₃ + CD₃OD): δ
1.23 (d, J=6.9 Hz, 12H)
3.20 (septet, J=6.9 Hz, 2H)
5.94 (d, J=2.3 Hz, 1H)
6.82 (s, 2H)
7.38 (d, J=2.3 Hz, 1H)
[Compound 36]

Str: R¹ = C(CH₃)₃, Ar = 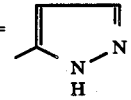
R² = CH(CH₃)₂,
R³ = H

M.p: 143–144.5° C.
¹H—NMR (CDCl₃ + CD₃OD): δ
1.23 (d, J=6.8 Hz, 6H)
1.41 (s, 9H)
3.12 (septet, J=6.8 Hz, 1H)
5.93 (d, J=2.4 Hz, 1H)
6.84 (d, J=2.6 Hz, 1H)
6.90 (d, J=2.6 Hz, 1H)
7.37 (d, J=2.4 Hz, 1H)
[Compound 37]

Str: R¹ = R² = R³ = CH₃, Ar = 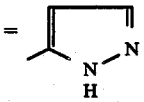

M.p.: 137–137.5° C. (decomp.)
¹H—NMR (CDCl₃ + CD₃OD): δ

TABLE 4-continued

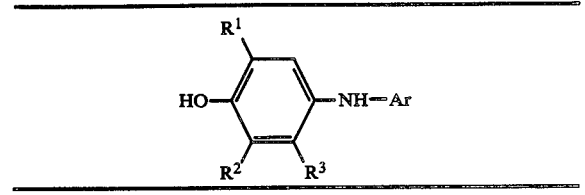

2.15 (s, 3H)
2.19 (s, 6H)
5.70 (broad s, 1H)
6.91 (s, 1H)
7.33 (broad s, 1H)
[Compound 38]

Str: $R^1 = R^2 = C(CH_3)_3$, Ar = 
$R^3 = H$

M.p: 129.5–131° C.
$^1H$—NMR (CDCl$_3$): δ
1.42 (s, 18H)
3.76 (s, 3H)
4.78 (s, 1H)
5.84 (d, J=2.3 Hz, 1H)
6.96 (s, 2H)
7.15 (d, J=2.3 Hz, 1H)
[Compound 39]

Str: $R^1 = R^2 = C(CH_3)_3$, Ar =
$R^3 = H$

M.p: 172–173° C.
$^1H$-NMR (CDCl$_3$): δ
1.41 (s, 18H)
3.72 (s, 3H)
4.84 (s, 1H)
5.17 (broad s, 1H)
5.90 (d, J = 2.0 Hz, 1H)
6.69 (s, 2H)
7.40 (d, J=2.0 Hz, 1H)
[Compound 40]

Str:
$R^1 = R^2 = C(CH_3)_3$, Ar =
$R^3 = H$

M.p: 117.5–118.5° C.
$^1H$—NMR (CDCl$_3$): δ
0.91 (t, J=7.0 Hz, 3H)
1.42 (s, 18H)
1.63–2.15 (m, 2H)
3.92 (t, J=6.9 Hz, 2H)
4.74 (s, 1H)
5.82 (d, J=2.3 Hz, 1H)
6.98 (s, 2H)
7.18 (d, J=2.3 Hz, 1H)
[Compound 41]

Str: $R^1 = R^2 = C(CH_3)_3$, Ar =
$R^3 = H$

M.p: 139.5–141° C. (decomp.)
$^1H$—NMR (CDCl$_3$): δ
0.92 (t, J=7.4 Hz, 3H)
1.40 (s, 18H)
1.65–2.05 (m, 2H)
3.97 (t, J=7.3 Hz, 2H)
4.78 (s, 1H), 4.95 (broad s, 1H)
5.90 (d, J=2.0 Hz, 1H)
6.67 (s, 2H)
7.42 (d, J=2.0 Hz, 1H)
[Compound 42]

TABLE 4-continued

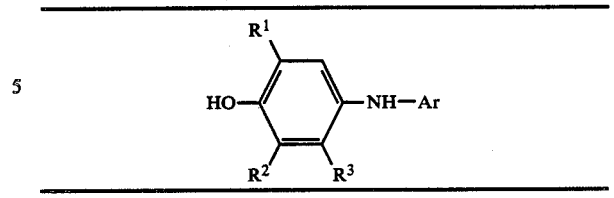

Str: $R^1 = R^2 = C(CH_3)_3$, Ar =
$R^3 = H$

M.p: 179–181° C.
$^1H$—NMR (CDCl$_3$): δ
1.41 (s, 18H)
3.76 (s, 3H)
4.83 (s, 1H), 5.12 (broad s, 1H)
6.21 (s, 1H), 6.75 (s, 2H)
7.24–7.62 (m, 3H)
7.70–7.85 (m, 2H)
[Compound 43]

Str:
$R^1 = R^2 = C(CH_3)_3$, Ar =
$R^3 = H$

M.p: 167–168° C.
$^1H$—NMR (CDCl$_3$): δ
1.43 (s, 18H)
4.92 (s, 1H)
5.45 (broad s, 1H)
6.28 (s, 1H), 6.94 (s, 2H)
7.25–7.90 (m, 10H)
[Compound 44]

Str:
$R^1 = R^2 = C(CH_3)_3$, Ar =
$R^3 = H$

M.p: 130–131° C.
$^1H$—NMR (CDCl$_3$): δ
1.34 (t, J=7.0 Hz, 3H)
1.40 (s, 18H)
3.39 (s, 3H)
4.28 (q, J=7.0 Hz, 2H)
5.06 (s, 1H)
6.75 (s, 2H)
7.42 (broad s, 1H)
7.74 (s, 1H)
[Compound 45]

Str: $R^1 = R^2 = C(CH_3)_3$, Ar =
$R^3 = H$

M.p: 188–189.5° C. (decomp.)
$^1H$—NMR (CDCl$_3$): δ
1.40 (s, 18H)
5.65 (broad s, 3H)
6.69 (s, 2H)
7.47 (s, 2H)

TABLE 4-continued

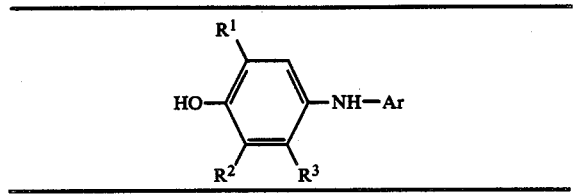

[Compound 46]

Str: $R^1 = R^2 = C(CH_3)_3$, Ar = 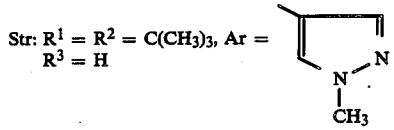
$R^3 = H$

M.p: 131-133° C.
$^1$H—NMR (CDCl$_3$): δ
1.40 (s, 18H), 3.86 (s, 3H)
4.66 (broad s, 1H)
6.67 (s, 2H)
7.22 (broad s, 1H), 7.36 (broad s, 1H)
[Compound 47]

Str: $R^1 = R^2 = C(CH_3)_3$, Ar = 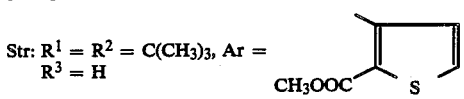
$R^3 = H$

M.p: 119.5-120.5° C.
$^1$H-NMR (CDCl$_3$): δ
1.43 (s, 18H), 3.86 (s, 3H)
5.03 (s, 1H), 6.87 (d, J=5.4 Hz, 1H)
7.01 (s, 2H), 7.30 (d, J=5.4 Hz, 1H)
8.54 (broad s, 1H)
[Compound 48]

Str: $R^1 = R^2 = C(CH_3)_3$, Ar = 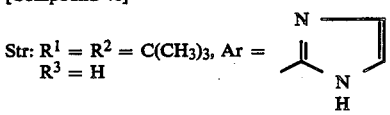
$R^3 = H$

M.p: 272-273° C. (decomp.)
$^1$H—NMR (CDCl$_3$): δ
1.41 (s, 18H), 5.23 (broad s, 1H)
6.58 (s, 2H), 7.01 (s, 2H)
9.25 (broad s, 1H)
[Compound 49]

Str: $R^1 = R^2 = C(CH_3)_3$, Ar = 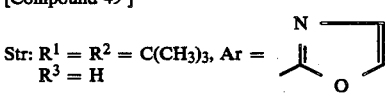
$R^3 = H$

M.p: 167.5-169.5° C. (decomp.)
$^1$H—NMR (CDCl$_3$): δ
1.45 (s, 18H), 6.87 (d, J=1.1 Hz, 1H)
7.22 (d, J=1.1 Hz, 1H)
7.23 (s, 2H)
[Compound 50]

Str: $R^1 = R^2 = C(CH_3)_3$, Ar = 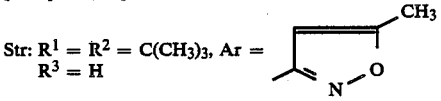
$R^3 = H$

M.p: 199-200° C. (decomp.)
$^1$H—NMR (CDCl$_3$): δ
1.43 (s, 18H)
2.31 (d, J=1 Hz, 3H)
4.92 (s, 1H)
5.66 (d like, J=1 Hz, 1H)
5.97 (broad s, 1H), 7.06 (s, 2H)
[Compound 51]

Str: $R^1 = R^2 = C(CH_3)_3$, Ar = 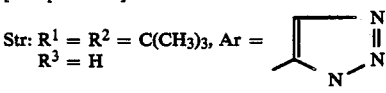
$R^3 = H$

M.p.: 190.5-191.5° C.
$^1$H—NMR (CDCl$_3$ + CD$_3$OD): δ
1.43 (s, 18H)
6.98 (s, 2H)
7.30 (s, 1H)
[Compound 52]

Str: $R^1 = R^2 = C(CH_3)_3$, Ar = 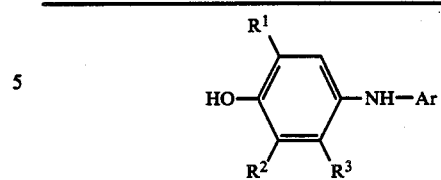
$R^3 = H$

M.p.: 207.5-209.5° C. (decomp.)
$^1$H—NMR (CDCl$_3$): δ
1.43 (s, 18H), 4.03 (s, 3H)
4.84 (s, 1H), 5.97 (broad s, 1H)
6.84 (s, 2H), 7.10 (s, 1H)
[Compound 53]

Str: $R^1 = R^2 = C(CH_3)_3$, Ar = 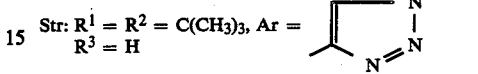
$R^3 = H$

M.p: 105-106.5° C.
$^1$H—NMR (CDCl$_3$): δ
1.43 (s, 18H), 4.05 (s, 3H)
4.84 (s, 1H), 5.70 (broad s, 1H)
6.95 (s, 2H), 7.18 (s, 1H)
[Compound 54]

Str: $R^1 = R^2 = C(CH_3)_3$, Ar = 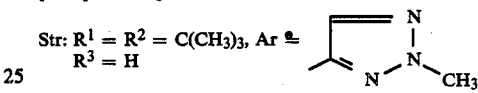
$R^3 = H$

M.p: 233-235° C. (decomp.)
$^1$H—NMR (CDCl$_3$ + CD$_3$OD): δ
1.44 (s, 18H)
7.17 (s, 2H)
7.68 (s, 1H)
[Compound 55]

Str: $R^1 = R^2 = C(CH_3)_3$, Ar = 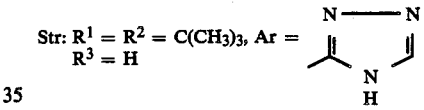
$R^3 = H$

M.p.: 150-151.5° C. (decomp.)
$^1$H—NMR (CDCl$_3$): δ
1.37 (s, 18H), 4.99 (s, 1H)
6.51 (s, 2H), 7.02 (broad s, 1H)
8.30 (s, 2H)
[Compound 56]

Str: $R^1 = R^2 = C(CH_3)_3$, Ar = 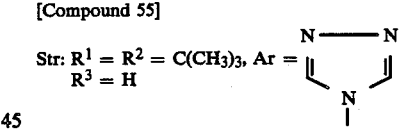
$R^3 = H$

M.p.: 240.5-242.5° C.
$^1$H—NMR (CDCl$_3$ + CD$_3$OD): δ
1.43 (s, 18H), 7.16 (s, 2H)
7.35-7.49 (m, 3H)
8.09-8.23 (m, 2H)
[Compound 57]

Str: $R^1 = R^2 = C(CH_3)_3$, Ar = 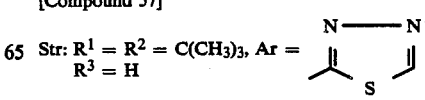
$R^3 = H$

M.p: 215.5-217.5° C.
$^1$H—NMR (CDCl$_3$ + CD$_3$OD): δ

TABLE 4-continued

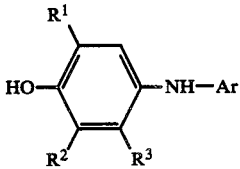

1.45 (s, 18H)
7.18 (s, 2H)
8.39 (s, 1H)
[Compound 58]

Str: R¹ = R² = C(CH₃)₃, Ar = (thiazole with CH₃)
R³ = H

M.p.: 231–232° C.
¹H—NMR (CDCl₃): δ
1.47 (s, 18H), 2.59 (s, 3H)
5.04 (broad s, 1H)
7.15 (s, 2H)
[Compound 59]

Str: R¹ = R² = C(CH₃)₃, Ar = (pyridazine)
R³ = H

M.p: 194.5–196° C.
¹H—NMR (CDCl₃): δ
1.46 (s, 18H), 5.09 (s, 1H)
7.43 (s, 2H), 8.06 (broad s, 1H)
8.18 (d, J=2.3 Hz, 1H)
8.62 (d, J=2.3 Hz, 1H)
[Compound 60]

Str: R¹ = R² = C(CH₃)₃, Ar = (dimethylpyridazine)
R³ = H

M.p: 243.5–245.5° C.
¹H—NMR (CDCl₃): δ
1.46 (s, 18H), 2.41 (s, 3H)
2.54 (s, 3H), 4.99 (s, 1H)
7.50 (s, 2H), 7.78 (broad s, 1H)
[Compound 61]

Str: R¹ = R² = C(CH₃)₃, Ar = (methylthiophene)
R³ = H
(hydrochloride)

M.p: 183–185° C. (decomp.)
¹H—NMR (DMSO-d₆): δ
1.33 (s, 18H), 2.25 (s, 3H)
6.66 (s, 2H)
6.89 (d, J=5.2 Hz, 1H)
7.19 (d, J=5.2 Hz, 1H)

EXAMPLE 62

Preparation of 2-N-(3,5-di-tert-butyl-4-hydroxyphenyl)aminopyrazine-4-oxide (Compound 62)

Step I

A 1.62 ml quantity of pyridine was dissolved in 60 ml of dichloroethane, and 0.55 ml of titanium tetrachloride was added thereto. The mixture was refluxed with heating for 15 minutes. To the mixture were added 2.20 g of 2,6-di-tert-butyl-1,4-benzoquinone and 1.11 g of 2-aminopyrazine-4-oxide, and the resulting mixture was refluxed with heating for 2 hours. The reaction mixture was cooled to room temperature and filtered through a Celite pad, and the insoluble materials were washed there with dichloromethane. The filtrate was concentrated and the resulting crude product was purified by silica gel column chromatography (eluent: diethyl ether-hexane=2:3), giving 0.65 g of 2-N-(3,5-di-tert-butyl-4-oxo-2,5-cyclohexadienylidene)aminopyrazine-4-oxide as a yellow solid.

Melting point: 152°–153° C.
¹H—NMR (CDCl₃): δ
1.23 (s, 9H), 1.32 (s, 9H), 6.82 (d, J=2.6 Hz, 1H), 6.98 (d, J=2.6 Hz, 1H), 7.93–7.95 (m, 2H), 8.32 (dd, J=3.5 Hz, 1.5 Hz, 1H).

Step II

A 0.50 g quantity of 2-N-(3,5-di-tert-butyl-4-oxo-2,5-cyclohexadienylidene)aminopyrazine-4-oxide was dissolved in 6 ml of tetrahydrofuran, and a solution of 4.8 g of sodium hydrosulfite in 18 ml of water was added thereto. The resulting mixture was stirred at room temperature for 1 hour. The solid precipitated was collected, washed with water and then with diethyl ether, and dried. The crude product was recrystallized from acetic acid-acetonitrile, giving 0.37 g of the title compound (Compound 62) as a pale yellow solid.

Table 5 below shows the structure and properties (melting point and ¹H—NMR spectrum data) of Compound 62.

EXAMPLE 63

Preparation of Compound 63

Following the general procedure of Step I of Example 62, and using 2,6-di-tert-butyl-1,4-benzoquinone and 3-amino-6-methylpyridazine-1-oxide as the starting materials, 3-N-(3,5-di-tert-butyl-4-oxo-2,5-cyclohexadienylidene)amino-6-methylpyridazine-1-oxide.

The resulting intermediate compound was subjected to the reduction reaction and purification in the same manner as Step II of Example 62, giving the compound listed in Table 5 below as "Compound 63" was prepared.

Table 5 shows the structure and properties (melting point and ¹H—NMR spectrum data) of Compound 63.

EXAMPLE 64

Preparation of 2-N-(3,5-di-tert-butyl-4-hydroxyphenyl)aminopyrazine-1-oxide (Compound 64).

Step I

In 1000 ml of dichloromethane were dissolved 30.0 g of 2,6-di-tert-butyl-4-pyrazinylimino-2,5-cyclohexadien-1-one (Compound 1a) and 25.0 g of 70% 3-chloroperoxybenzoic acid, and the solution was stirred at room temperature for 15 hours. The reaction mixture was poured into a 5% aqueous solution of sodium bicarbonate. The organic layer was separated and the aqueous layer was extracted with dichloromethane. The organic layers were combined, washed with a 5% aqueous solution of sodium bicarbonate and then with water, dried over magnesium sulfate and concentrated. The resulting crude product was purified by silica gel column chromatography (eluent: diethyl ether-hexane=1:1→diethyl ether→ethyl acetate), giving 9.0 g of 2-N-(3,5-di-tert-butyl-4-oxo-2,5-cyclohexadienylidene)aminopyrazine-4-oxide (the same product as prepared in Step I of Example 62) and 1.8 g of 2-N-(3,5-di-tert-butyl-4-oxo-2,5-cyclohexadienylidene)aminopyrazine-1-oxide. The 1-oxide has the following properties.

Melting point: 165°–167° C.

$_1$H—NMR (CDCl$_3$): δ
1.23 (broad s, 9H), 1.33 (broad s, 9H), 6.54 (broad s, 1H), 7.16 (broad s, 1H), 8.14 (broad s, 1H), 8.24 (dd, J=4.1 Hz, 0.7 Hz, 1H), 8.29 (d, J=4.1 Hz, 1H).

Step II

From 2-N-(3,5-di-tert-butyl-4-oxo-2,5-cyclohexadienylidene)aminopyrazine-1-oxide obtained above, the title compound (Compound 64) was prepared following the general procedure of Step II of Example 62.

Table 5 below shows the structure and properties (melting point and $^1$H—NMR spectrum data) of Compound 64.

TABLE 5

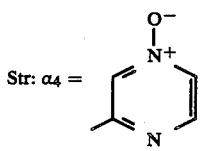

[Compound 62]

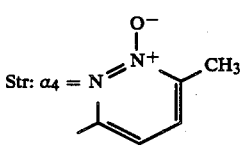

M.P.: 265.5–266.5° C. (decomp.)
$^1$H—NMR (DMSO—d$_6$): δ
1.38 (s, 18H), 6.75 (s, 1H)
7.33 (s, 2H)
7.56 (dd, J=4.1 Hz, 1.2 Hz, 1H)
7.64 (d, J=1.2 Hz, 1H)
7.99 (d, J=4.1 Hz, 1H)
9.11 (s, 1H)
[Compound 63]

Str: α$_4$ =

M.P.: 255–256° C. (decomp.)
$^1$H—NMR (DMSO—d$_6$): δ
1.39 (s, 18H), 2.22 (s, 3H)
6.60 (d, J=8.7 Hz, 1H)
6.72 (s, 1H), 7.29 (s, 2H)
7.52 (d, J=8.7 Hz, 1H)
8.94 (s, 1H)
[Compound 64]

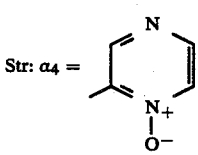

M.P.: 231–233° C.
$^1$H—NMR (DMSO—d$_6$): δ
1.39 (s, 18H), 6.99 (s, 1H)
7.09 (s, 2H)
7.84 (d, J=4.0 Hz, 1H)
8.21 (d, J=0.7 Hz, 1H)
8.28 (dd, J=4.0 Hz, 0.7 Hz, 1H)
8.97 (s, 1H)

Described below are the results of pharmacological test conducted with use of the compounds of the invention.

(1) Anti-inflammatory activity: inhibition of carrageenin-induced paw edema in rats The compound was tested for the above activity according to the method of C.A. Winter et al. [Proc. Soc. Exp. Biol. Med., 111, 544 (1962)] using male rats of S.D. strain (170 to 190 g, fasted), five rats in each group.

One hour after the test compound was orally given to the animal, 0.1 ml of 1% carrageenin solution was subcutaneously injected into the right footpad. The paw volume was measured 3 hours thereafter, and the resulting increase in the volume was calculated based on the volume before the injection of carrageenin solution. The percent inhibition was determined in comparison with the increase in the control group.

The results are shown below in Table 6 in which the values in parentheses are dosage of the test compounds.

TABLE 6

| Compound No. | Inhibition percent of edema (%) (mg/kg p.o.) |
|---|---|
| 1 | 37 ( 50) |
| 4 | 39 (100) |
| 10 | 35 ( 25) |
| 11 | 62 (100) |
| 12 | 29 ( 25) |
| 13 | 41 ( 10) |
| 14 | 30 ( 50) |
| 15 | 16 (100) |
| 16 | 10 (100) |
| 17 | 36 ( 25) |
| 18 | 36 ( 50) |
| 22 | 32 (100) |
| 24 | 31 ( 25) |
| 25 | 15 (100) |
| 26 | 27 (100) |
| 27 | 33 (100) |
| 28 | 33 (100) |
| 33 | 46 (100) |
| 34 | 65 (100) |
| 39 | 46 (100) |
| 48 | 63 ( 25) |
| 49 | 41 (100) |
| 50 | 12 ( 50) |
| 51 | 42 (100) |
| 54 | 20 (100) |
| 55 | 23 (100) |
| 56 | 13 (100) |
| 58 | 30 (100) |
| 59 | 37 ( 50) |
| 61 | 25 ( 50) |
| 64 | 31 ( 25) |
| Indomethacin | 36 ( 5) |

| Preparation Example 1 | |
|---|---|
| Compound 1 | 200 mg |
| Glucose | 250 mg |
| Distilled water for injection | Adequate amount |
| Total | 5 ml |

In the distilled water for injection was dissolved the Compound 1 and glucose, and the resulting solution was placed in a 5 ml ampoule. The air in the ampoule was replaced by nitrogen gas. The preparation was sterilized by heating at 121° C. for 15 minutes, giving an injection solution having the above composition.

| Preparation Example 2 | |
|---|---|
| Compound 1 | 100 g |
| Crystalline cellulose (Trademark "Avicel PH101" product of Asahi Chemical Industry Co., Ltd., Japan) | 40 g |
| Corn starch | 30 g |
| Magnesium stearate | 2 g |
| Total | 172 g |
| Hydroxypropyl methyl cellulose (Trademark "TC-5", product of Shin-etsu Kagaku Kogyo Kabushiki Kaisha, Japan) | 10 g |
| Polyethylene glycol 6000 | 3 g |
| Pigment | 0.3 g |
| Titanium dioxide | 0.2 g |
| Water | 86.5 g |
| Total | 100 g |

The foregoing Compound 1, Crystalline cellulose, Corn starch and magnesium stearate were ground and formulated into tablets with use of sugar-coated punch having a radius of 8 mm. The resulting tablets were coated with a film coating agent consisting of hydroxypropyl methyl cellulose, polyethylene glycol 6000, castor oil and ethanol, giving film-coated tablets having the above composition.

| Preparation Example 3 | |
|---|---|
| Compound 59 | 2 g |
| Purified lanolin | 5 g |
| Bleached bees wax | 5 g |
| White petrolatum | 88 g |
| Total | 100 g |

The bleached bees wax was melted by heating, and thereto were added Compound 59, purified lanolin and white petrolatum. The mixture was heated until it become liquid, and then stirred until it solidified, giving an ointment having the above composition.

We claim:

1. A p-aminophenol compound of the formula

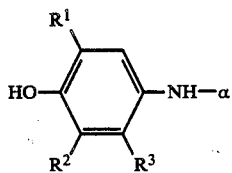

(1)

wherein:
R1 is a lower alkyl group;
R2 is a hydrogen atom or a lower alkyl group;
R3 is a hydrogen atom or a lower alkyl group; or
R2 and R3 taken together may represent a group —(CH2)4— or a group —CH=CH—CH=CH—; and
α is pyrazinyl or a pyrazine-N-oxide ring, each having 1 to 3 substitutents selected from the group consisting of a lower alkyl group, halogen atom, phenyl group, lower alkoxycarbonyl group, amino group, lower alkoxy group and hydroxy-lower alkyl group,
or a pharmaceutically acceptable salt thereof.

2. A compound as defined in claim 1, which is represented by the formula

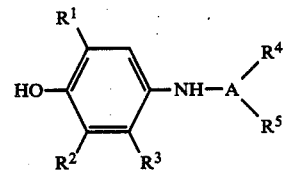

(1-1)

wherein:
R1, R2 and R3 are defined in claim 14;
A is pyrazinyl or a pyrazine-N-oxide ring;
R4 is a hydrogen atom, a lower alkyl group or a halogen atom; and
R5 is a hydrogen atom, a lower alkyl group, halogen atom, phenyl group, lower alkoxycarbonyl group, amino group, lower alkoxy group of hydroxy-lower alkyl group;
or a pharmaceutically acceptable salt thereof.

3. A compound as defined in claim 2, which is represented by the formula

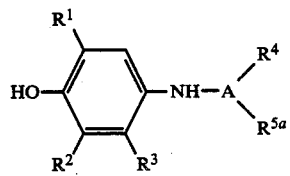

(1-1A)

wherein R2 is a lower alkyl group, R3 is a hydrogen atom, A is pyrazinyl or a pyrazine-N-oxide ring and R5a is a hydrogen atom, lower alkyl group, halogen atom, amino group, lower alkoxy group or hydroxylower alkyl group,
or a pharmaceutically acceptable salt thereof.

4. A compound as defined in claim 3, which is selected from the group consisting of:
2,6-di-tert-butyl-4-pyrazinylaminophenol,
2-isopropyl-6-tert-butyl-4-pyrazinylaminophenol, and
2-N-pyrazine-1-oxide.

5. A compound as defined in claim 1, which is represented by the formula

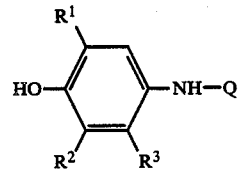

(1-3)

wherein R1 and R2 each represents a lower alkyl group, R3 is a hydrogen atom, and Q is a substituted or unsubstituted pyrazinyl group wherein the substituent is a lower alkyl group or lower alkoxy group.

6. An anti-inflammatory composition comprising an anti-inflammation effective amount of the compound of claim 1 or a pharmaceutically acceptable salt thereof in combination with a pharmaceutically acceptable carrier or excipient therefor.

7. A pharmaceutical composition for inhibiting lipoxygenase, comprising a lipoxygenase inhibition effective amount of the compound of claim 1 or a pharmaceutically acceptable salt thereof in combination with a pharmaceutically acceptable carrier or excipient therefor.

8. A method for treating inflammation in a patient, comprising administering to said patient an antiinflammation effective amount of the compound of claim 1 or a pharmaceutically acceptable salt thereof.

* * * * *